US009625409B1

(12) United States Patent
Cai et al.

(10) Patent No.: US 9,625,409 B1
(45) Date of Patent: *Apr. 18, 2017

(54) ULTRA-SENSITIVE BIOSENSOR BASED ON LATERAL BIPOLAR JUNCTION TRANSISTOR HAVING SELF-ALIGNED EPITAXIALLY GROWN BASE

(71) Applicant: International Business Machines Corporation, Armonk, NY (US)

(72) Inventors: Jin Cai, Cortlandt Manor, NY (US); Tak H. Ning, Yorktown Heights, NY (US); Jeng-Bang Yau, Yorktown Heights, NY (US); Sufi Zafar, Briarcliff Manor, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/040,976

(22) Filed: Feb. 10, 2016

Related U.S. Application Data

(63) Continuation of application No. 15/019,718, filed on Feb. 9, 2016.

(51) Int. Cl.
*G01N 27/26* (2006.01)
*H01L 29/06* (2006.01)
(Continued)

(52) U.S. Cl.
CPC ......... *G01N 27/26* (2013.01); *H01L 29/0649* (2013.01); *H01L 29/1008* (2013.01); *H01L 29/6625* (2013.01); *H01L 29/735* (2013.01)

(58) Field of Classification Search
CPC ... G01N 27/26; H01L 29/1008; H01L 29/735; H01L 29/6625; H01L 29/0649
See application file for complete search history.

(56) References Cited

U.S. PATENT DOCUMENTS 5,225,374 A * 7/1993 Fare .................. G01N 27/3277
204/416
7,692,219 B1 4/2010 Holm-Kennedy
(Continued)

OTHER PUBLICATIONS

K.B. Pairzi et al., "An internally Amplified Signal SOI Nano-bridge Biosensor for Electrical Detection of DNA Hybridazation", IEEE, SOI IEEE Conference, 2009 IEEE International, pp. 1-2.*
(Continued)

*Primary Examiner* — William Coleman
(74) *Attorney, Agent, or Firm* — Louis J. Percello, Esq.; Otterstedt, Ellenbogen & Kammer, LLP

(57) ABSTRACT

An exemplary biosensor sensor for detecting the presence of a biological material includes an SOI substrate, a lateral BJT formed on at least a portion of the substrate, and a sensing structure formed on at least a portion of an upper surface of the BJT. The BJT includes an emitter region, a collector region and a base region, the base region being formed between the emitter and collector regions and laterally adjacent thereto. The sensing structure includes at least one dielectric layer contacting at least a portion of the base region. The dielectric layer forms a receptacle for confining a biological molecule being tested and is configured to respond to charges in biological molecules, the charges being converted to a sensing signal by the BJT.

20 Claims, 14 Drawing Sheets

(51) Int. Cl.
    *H01L 29/735*  (2006.01)
    *H01L 29/66*   (2006.01)
    *H01L 29/10*   (2006.01)

(56) References Cited

U.S. PATENT DOCUMENTS

| | | | |
|---|---|---|---|
| 8,835,984 B2 * | 9/2014 | Ren | G01N 27/414 |
| | | | 257/194 |
| 8,980,667 B2 | 3/2015 | Cai et al. | |
| 9,040,929 B2 | 5/2015 | Cai et al. | |
| 9,059,195 B2 | 6/2015 | Cai et al. | |
| 2005/0205891 A1 | 9/2005 | Holm-Kennedy | |
| 2010/0117165 A1 * | 5/2010 | Fiorillo | C01B 39/00 |
| | | | 257/414 |
| 2012/0138460 A1 | 6/2012 | Baghbani-Parizi et al. | |
| 2012/0223293 A1 | 9/2012 | Borenstein et al. | |
| 2013/0158378 A1 | 6/2013 | Berger et al. | |
| 2016/0153932 A1 * | 6/2016 | Eklund | G01N 27/414 |
| | | | 257/253 |

OTHER PUBLICATIONS

USPTO Form PTO-892 issued in parent U.S. Appl. No. 15/019,718; mailed date Nov. 29, 2016.

* cited by examiner

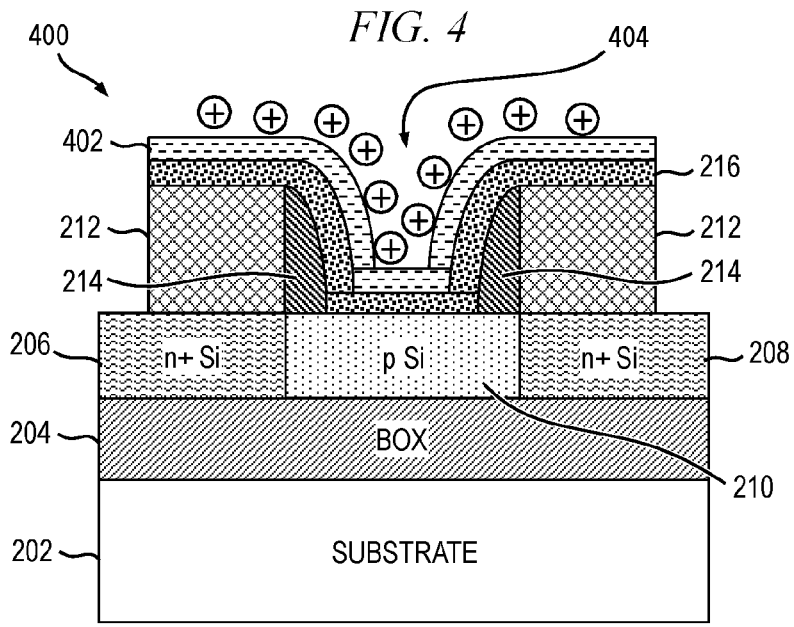
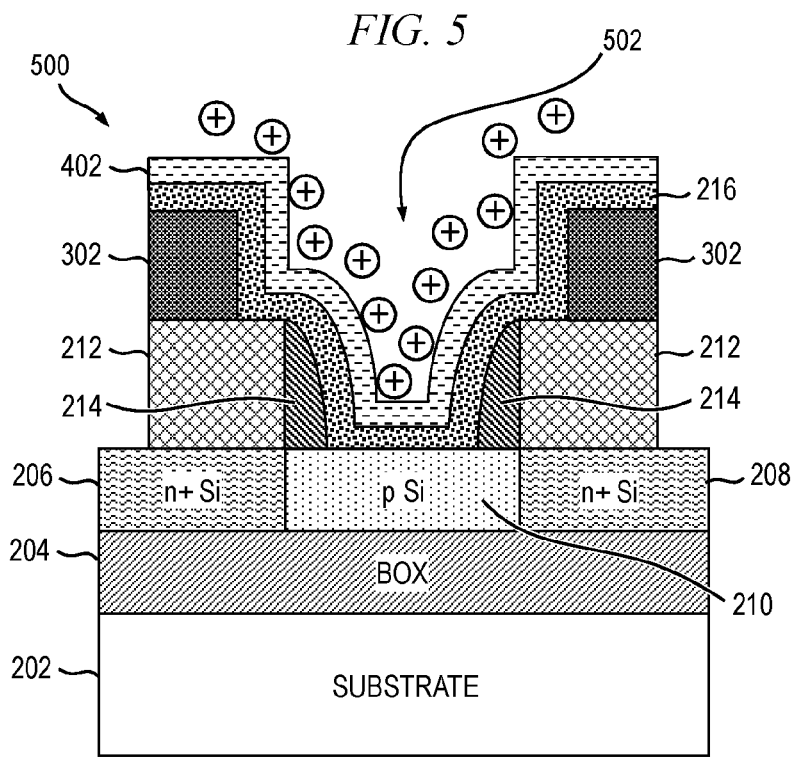

FIG. 12A
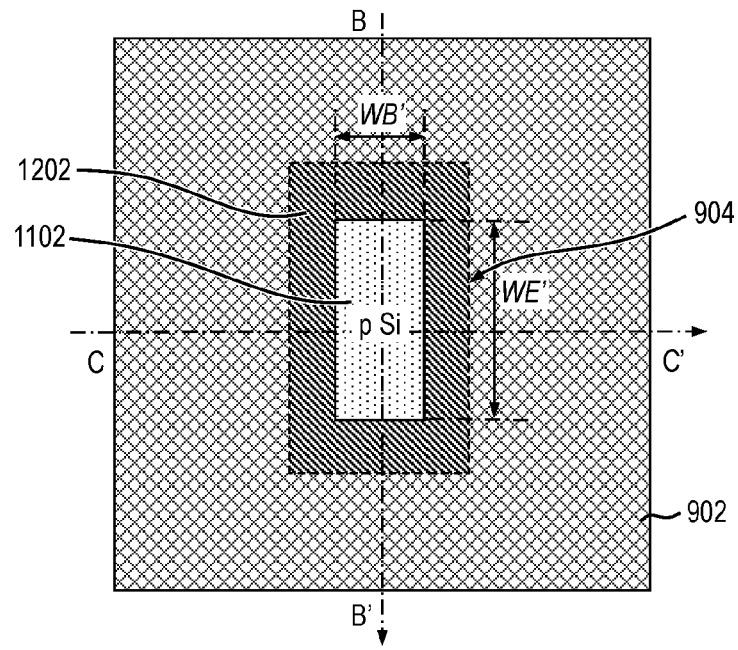
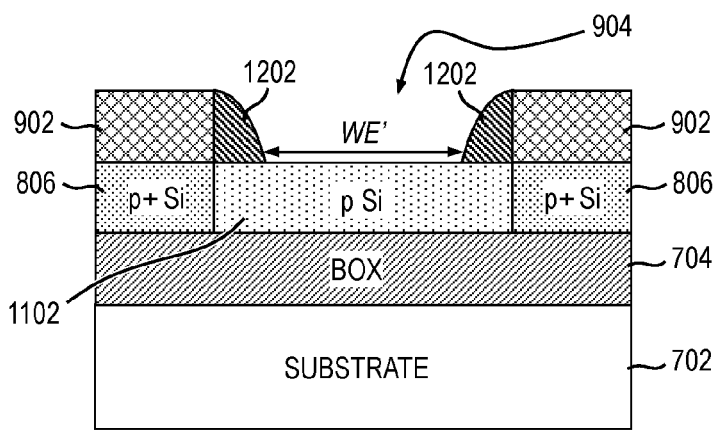
FIG. 12B
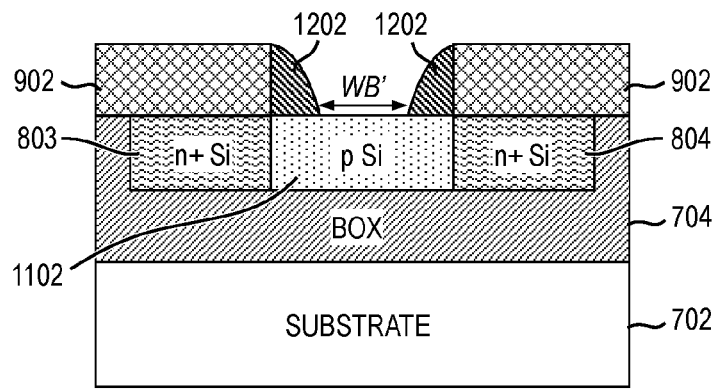
FIG. 12C

ULTRA-SENSITIVE BIOSENSOR BASED ON LATERAL BIPOLAR JUNCTION TRANSISTOR HAVING SELF-ALIGNED EPITAXIALLY GROWN BASE

CROSS-REFERENCE TO RELATED APPLICATION(S)

The present application is a continuation of U.S. patent application Ser. No. 15/019,718, filed Feb. 9, 2016, having the same title and inventors as the present application, the disclosure of which is expressly incorporated by reference herein in its entirety for all purposes.

BACKGROUND

The present invention relates generally to the electrical, electronic and computer arts, and, more particularly, to integrated sensors.

Advancements in microelectronics have facilitated the introduction of numerous applications that improve the quality of life and benefit society in immeasurable ways. In addition to mainstream applications in conventional consumer electronics, microelectronics can be utilized in seemingly remote areas of the population. Given the ever-increasing globalization of society, precise acquisition, real-time (or near real-time) processing and analyses of tremendous amounts of information are in high demand. One example is the use of biosensors that can detect and provide relevant environmental information, such as, but not limited to, radiation levels, inorganic particles, biological entities, etc., to ensure safety, security, and stability of environmental control. In addition, with advancements in mobile technology, technological benefits have been achieved by integrating such biosensors into personal devices to provide real-time and customized readout of information.

Conventionally, different types of biosensors are fabricated for the detection of corresponding different types of materials/substances. For example, Geiger counters are used to detect radiation dose, using ionization produced in a Geiger-Müller tube, and provide a real-time and semi-quantitative readout. However, Geiger counters have limited success in measuring high radiation rates and in measuring the energy of incident radiation. Personal radiation dosimeters in the form of wearable badges and the like are available but cannot provide a real-time indication of radiation; rather, such personal radiation dosimeters provide an indication of accumulated radiation or total radiation dose received. Biosensors, which often combine a biological component with a physicochemical detector, depending on the type of material to be detected, often require a certain amount of time for readout due to the reaction/detection mechanism. Moreover, better resolution/sensitivity requires longer processing time, which sometimes involves special instruments only available in laboratories, thus limiting the portability of biosensors.

SUMMARY

Principles of the invention, in accordance with one or more embodiments thereof, provide techniques for forming to a monolithic biosensor for detecting the presence of biological entities, and methods for making said biosensor.

In accordance with an embodiment of the invention, a biosensor sensor for detecting the presence of a biological material includes a silicon-on-insulator (SOI) substrate, a bipolar junction transistor (BJT) formed on at least a portion of the substrate, and a sensing structure formed on at least a portion of an upper surface of the BJT. The BJT includes an emitter region, a collector region and a self-aligned epitaxially grown intrinsic base region laterally adjacent to the emitter and collector regions. The sensing structure includes an opening, centered above and exposing the intrinsic base region, and at least one dielectric layer formed in the opening and contacting at least a portion of the intrinsic base region. The dielectric layer is configured to respond to charges in biological molecules, the charges being converted to a sensing signal by the BJT.

In accordance with another embodiment, a biosensor for detecting the presence of a biological material includes an SOI substrate, a lateral BJT formed on at least a portion of the substrate, and a sensing structure formed on at least a portion of an upper surface of the BJT. The BJT includes an emitter region, a collector region and a base region, the base region being formed between the emitter and collector regions and laterally adjacent thereto. The sensing structure includes at least one dielectric layer contacting at least a portion of the base region. The dielectric layer forms a conically-shaped receptacle and is configured to respond to charges in biological molecules, the charges being converted to a sensing signal by the BJT.

In accordance with yet another embodiment, a method for detecting the presence of a biological material includes the steps of: forming a lateral BJT on at least a portion of an SOI substrate, the BJT including an emitter region, a collector region and a self-aligned epitaxially grown intrinsic base region adjacent to the emitter and collector regions; and forming a sensing structure on at least a portion of an upper surface of the BJT, the sensing structure including an opening, centered above and exposing the intrinsic base region, and at least one dielectric layer formed in the opening and contacting at least a portion of the intrinsic base region, the dielectric layer being configured to respond to charges in biological molecules.

As used herein, "facilitating" an action includes performing the action, making the action easier, helping to carry the action out, or causing the action to be performed. Thus, by way of example only and without limitation, in the context of a processor-implemented method, instructions executing on one processor might facilitate an action carried out by instructions executing on a remote processor, by sending appropriate data or commands to cause or aid the action to be performed. For the avoidance of doubt, where an actor facilitates an action by other than performing the action, the action is nevertheless performed by some entity or combination of entities.

One or more embodiments of the invention or elements thereof can be implemented in the form of a computer program product including a computer readable storage medium with computer usable program code for performing the method steps indicated. Furthermore, one or more embodiments of the invention or elements thereof can be implemented in the form of a system (or apparatus) including a memory, and at least one processor that is coupled to the memory and operative to perform exemplary method steps. Yet further, in another aspect, one or more embodiments of the invention or elements thereof can be implemented in the form of means for carrying out one or more of the method steps described herein; the means can include (i) hardware module(s), (ii) software module(s) stored in a computer readable storage medium (or multiple such media) and implemented on a hardware processor, or (iii) a combination of (i) and (ii); any of (i)-(iii) implement the specific techniques set forth herein.

Techniques of the present invention can provide substantial beneficial technical effects. By way of example only and without limitation, a biosensor according to one or more embodiments of the invention may provide one or more of the following advantages:

planar base sensing contact, thus enabling high device density;

"conically-shaped" sensing structure renders more effective confinement of materials being tested, especially liquids/droplets, and increases sensing signal;

readily integratable with micro/nano fluidics modules and devices;

elimination of reference electrode, which is a major limitation in the miniaturization of the sensor.

These and other features and advantages of the present invention will become apparent from the following detailed description of illustrative embodiments thereof, which is to be read in connection with the accompanying drawings.

BRIEF DESCRIPTION OF THE SEVERAL VIEWS OF THE DRAWINGS

The following drawings are presented by way of example only and without limitation, wherein like reference numerals (when used) indicate corresponding elements throughout the several views, and wherein:

FIGS. 2 through 5 are cross-sectional views depicting at least a portion of exemplary monolithic biosensors including a lateral silicon-on-insulator (SOI) BJT structure, according to embodiments of the present invention;

FIGS. 7A through 14B are top plan and cross-sectional views depicting exemplary processing steps/stages in the fabrication of exemplary biosensors, comprising a lateral SOI BJT structure, according to embodiments of the present invention;

It is to be appreciated that elements in the figures are illustrated for simplicity and clarity. Common but well-understood elements that may be useful or necessary in a commercially feasible embodiment may not be shown in order to facilitate a less hindered view of the illustrated embodiments.

DETAILED DESCRIPTION

Principles of the present invention will be described herein in the context of illustrative silicon-based biosensors that include a lateral bipolar junction transistor (BJT) structure integrally formed with a unique sensing structure. The lateral BJT in each of biosensors includes a planar base sensing contact, thus enabling high device density. The biosensors according to one or more embodiments are fabricated using a complementary metal-oxide-semiconductor (CMOS) process, thereby allowing the biosensors to be readily integrated with standard CMOS control and/or processing circuitry. It is to be appreciated, however, that the invention is not limited to the specific devices and/or methods illustratively shown and described herein. Rather, aspects of the present disclosure relate more broadly to a monolithic biosensor based on bipolar transistor operation, and methods for making said biosensor, which includes a sensing structure uniquely shaped to render more effective confinement of materials being tested, especially liquids/droplets, and to increase sensing signal. Moreover, it will become apparent to those skilled in the art given the teachings herein that numerous modifications can be made to the embodiments shown that are within the scope of the claimed invention. That is, no limitations with respect to the embodiments shown and described herein are intended or should be inferred.

Figure 1:
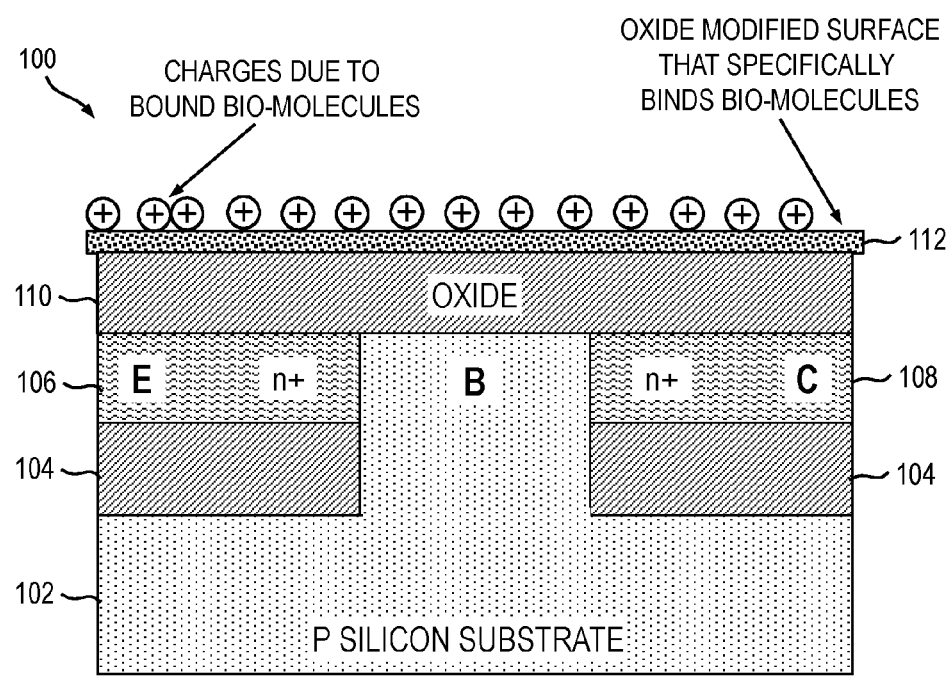
FIG. 1 is a cross-sectional view depicting a standard biosensor based on an inverted lateral bipolar junction transistor (BJT) structure.

FIG. 1 is a cross-sectional view depicting a standard biosensor 100 based on an inverted lateral BJT structure. The biosensor 100 includes a silicon substrate 102 which is doped to be of p-type conductivity. Emitter (E) and collector (C) regions, 106 and 108, respectively, are formed on an insulating layer 104 in defined areas (e.g., wells) in the substrate 102. The emitter and collector regions 106, 108, which are doped to be of n-type conductivity, are separated laterally from one another by a portion of the p-type substrate. The portion of the substrate 102 separating the emitter and collector regions 106, 108 serves as a p-type base (B) which, in conjunction with the n-type emitter and collector regions, forms the lateral BJT structure.

Contact to the p-type base is provided by the p-type substrate 102. Electrical contact to the p-type substrate 102 can be provided via the back-side of the p-type substrate, for the case where the p-type substrate is part of the starting wafer for device fabrication. Alternatively, electrical contact to the p-type substrate can be provided from the front-side via a p-type reach-through region (not explicitly shown) which extends from a top surface of the device structure down to the p-type substrate 102.

The biosensor 100 further includes a planar sensing layer 112 formed on an upper surface of the lateral BJT structure. An oxide layer 110 is formed between the sensing layer 112 and the BJT structure to electrically isolate the BJT structure from the planar sensing layer. The sensing layer 112 comprises an oxide-modified surface which specifically binds bio-molecules. The BJT structure is able to detect charges due to bound bio-molecules present on the sensing layer 112.

Several disadvantages are associated with this biosensor 100. For example, due to the arrangement of the inverted lateral BJT structure, a substrate contact (i.e., contact to p-type substrate 102) is required for setting an emitter-base bias voltage, which significantly limits device density and increases noise due to poor substrate isolation. Additionally, the planar (i.e., flat) shape of the sensing layer 112 renders it difficult to effectively confine biological materials being tested, particularly liquids/droplets. Furthermore, due to the relatively flat shape of the sensing layer 112, only the charge located directly above the base region induces a corresponding image charge in the base, which in turn induces a sensing signal. The charge located directly above the emitter induces a corresponding image charge in the emitter, and the charge located directly above the collector induces a corresponding image charge in the collector. Therefore, the charges located directly above emitter and collector do not contribute to the sensing signal. As will be explained in further detail in conjunction with FIG. 2, the "conically-shaped" (e.g., funnel-shaped or tapered) sensing structure of the biosensor according to one or more aspects of the present invention enables charges present on the sensing structure not directly above the base to contribute to the sensing signal.

Aspects of the invention advantageously eliminate or reduce one or more of the above-noted disadvantages of standard biosensors. One or more embodiments of the invention provide a biosensor based on a lateral silicon-on-insulator (SOI) BJT including a self-aligned epitaxially grown intrinsic base having a planar base/sensing contact, thereby increasing device density and thus allowing more sensors to be fabricated on a given wafer. One or more embodiments further include a sensing structure beneficially configured to provide a more effective confinement of materials being tested, especially liquids/droplets, and to increase the sensing signal. Moreover, a biosensor according to one or more embodiments is readily integratable with micro and nanofluidics modules and/or devices.

By way of example only and without limitation, FIGS. 2 through 5 are cross-sectional views depicting at least a portion of exemplary monolithic biosensors including a lateral SOI BJT structure, according to embodiments of the present invention. Specifically, with reference to FIG. 2, a biosensor 200 comprises a lateral SOI BJT structure including a substrate 202 on which a buried oxide (BOX) layer 204 is formed. A silicon layer 205, which may be referred to herein as an SOI layer, is formed on at least a portion of an upper surface of the BOX layer 204. Laterally-spaced regions 206 and 208 of n+ conductivity type formed in the SOI layer 205, proximate an upper surface of the SOI layer, form an emitter (E) and a collector (C), respectively, of the SOI BJT structure. A region 210 of p-type conductivity is formed in the upper surface of the SOI layer 205 between the emitter and collector regions 206 and 208. The P region 210, which essentially forms an intrinsic base (B) of the SOI BJT structure, is laterally adjacent to the n+ regions 206, 208 thereby forming respective base-emitter and base-collector p-n junctions.

The biosensor 200 further comprises a sensing structure integrally formed on the upper surface of the BJT structure and electrically coupled with the intrinsic base region 210. The sensing structure includes insulating structures 212 which are formed on at least a portion of the upper surface of the BJT structure, proximate the emitter and collector regions 206, 208. The insulating structures 212 may be formed by patterning an insulating layer, using standard lithographic processing, and etching the insulating layer to define an opening therethrough for exposing the intrinsic base region 210. Dielectric spacers 214 are formed on sidewalls of the insulating structures 212 defining the intrinsic base region opening.

A dielectric layer 216, which in one or more embodiments comprises an oxide, is deposited on at least a portion of the upper surface of the biosensor 200 (that is, over the insulating structures 212, the sidewall spacers 214 and the exposed intrinsic base region 210. A profile of the dielectric layer 216 is configured to be conically-shaped (e.g., tapered or "funnel-shaped") by virtue of the insulating structures 212 and spacers 214 upon which the dielectric layer is formed, which beneficially serves as a receptacle 218 (i.e., containing structure) for providing a more effective confinement of bio-materials being tested/detected, especially liquids and/or droplets. The dimensions and shape of the insulating structures 212 and sidewall spacers 214 (e.g., thickness) will determine the profile of the dielectric layer 216, including a depth of the receptacle 218. It is to be appreciated that embodiments of the invention are not limited to any specific dimensions and shapes of the insulating structures 212 and spacers 214, and thus the dielectric layer 216. A surface property of the dielectric layer 216 is configured to make it sensitive to bio-molecules. Specifically, the dielectric layer 216 is modified, in one or more embodiments, to bind to bio-molecules. The intrinsic base region 210 is adapted to cause a sensing current to flow from the emitter to the collector which varies as a function of charges generated by bound bio-molecules present on the surface of the modified dielectric layer 216.

Charges generated by bound bio-molecules located directly above the intrinsic base region 210, including those charges located on the part of the modified dielectric layer 216 on the spacer 214, induce corresponding image charges in the intrinsic base region, resulting in an increase in the electron current flowing from the emitter 206 to the collector 208. The charges generated by bound bio-molecules located elsewhere, for example above emitter 206 and/or collector 208, are generally too far away from the intrinsic base region 210 to contribute effectively to the electron current flowing from emitter 206 to collector 208. In one or more embodiments, the dielectric layer 216 is a composite structure or film including a plurality of material layers. For example, in a tri-layer embodiment, the dielectric layer 216 comprises a bottom dielectric (e.g., oxide) layer, a top dielectric layer, and an electrically conductive layer sandwiched between the top and bottom dielectric layers, the top dielectric layer being modified to bind to bio-molecules. In this embodiment, all the charges generated by bound bio-molecules located on the top dielectric layer form image charges in the electrically conductive middle layer, which in turn form corresponding image charges in the intrinsic base region 210. Thus, all the charges generated by bound bio-molecules located on the top dielectric layer contribute effectively to increasing the electron current flowing from the emitter 206 to the collector 208.

Figure 2:
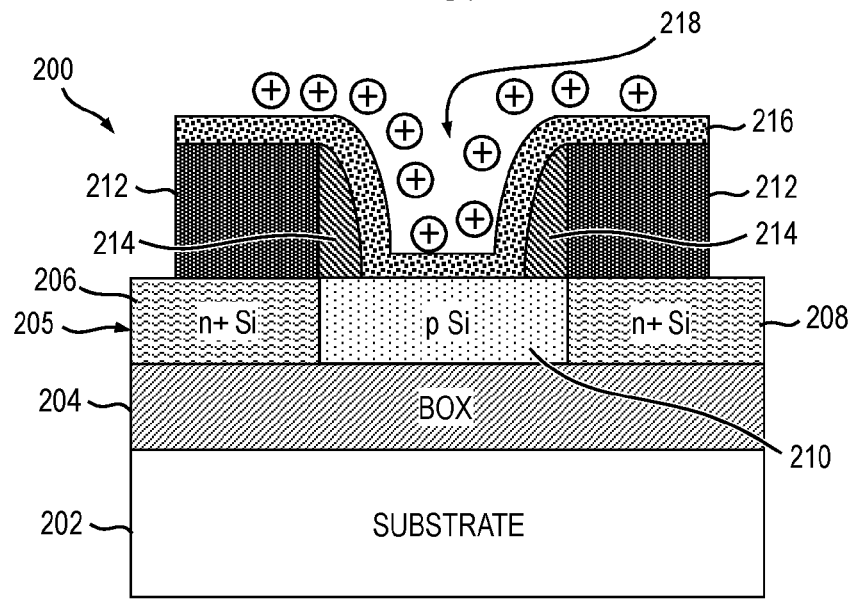
Figure 3:
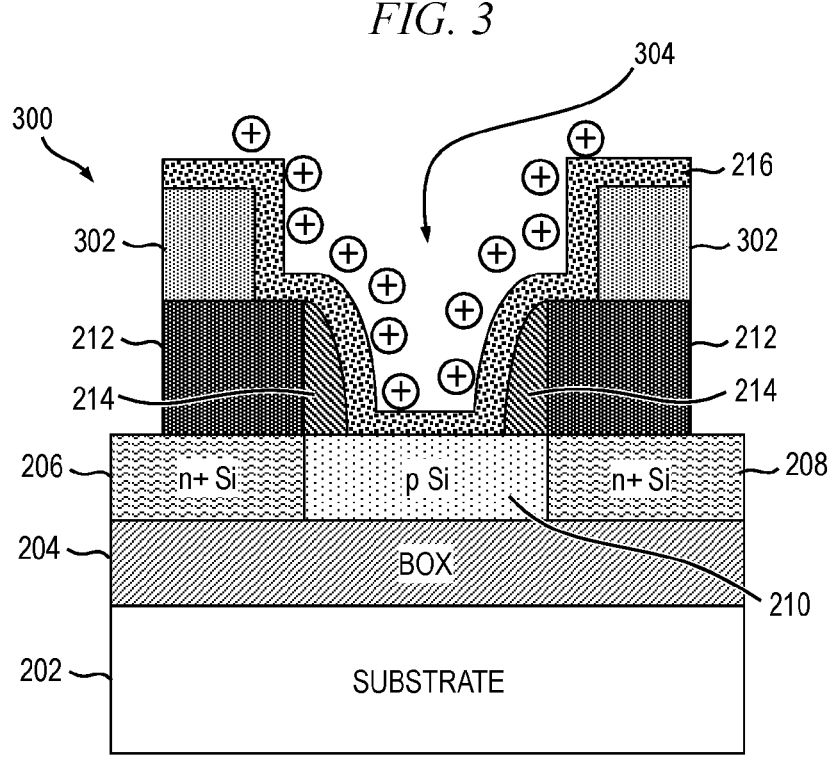

FIG. 3 is a cross-sectional view depicting at least a portion of an exemplary biosensor 300, according to another embodiment of the invention. The biosensor 300 comprises a lateral SOI BJT structure which is formed in manner consistent with the BJT structure of the biosensor 200 shown in FIG. 2. Specifically, the biosensor 300 includes a lateral SOI BJT structure, including n-type emitter and collector regions 206, 208 and a p-type intrinsic base region 210 between and laterally adjacent to the emitter and collector regions, formed on an SOI substrate (comprising BOX layer 204 and substrate 202). The biosensor 300 further includes a sensing structure that is modified slightly compared to the sensing structure of the biosensor 200 of FIG. 2. Specifically, with reference to FIG. 3, the sensing structure of the biosensor 300 includes second insulating structures 302 formed on at least a portion of the upper surface of the insulating structures 212. This second level of insulating structures 302 results in a dielectric layer 216 that exhibits a more stepped profile and a deeper receptacle 304 for confining a larger volume of bio-molecules being tested.

Many metallic ions, such as, for example, potassium ions ($K^+$) and sodium ions ($Na^+$), can diffuse inside silicon oxide. Among metallic ions, sodium ions diffuse most rapidly into and through silicon oxide, causing the device characteristics to change. Many biological solutions contain large amounts of sodium chloride (NaCl), where sodium ions can penetrate into the oxide sensing layer (e.g., 216 in FIGS. 2 and 3) of the sensing structure, thereby causing long-term drift issues. In order to reduce the drift effect caused by sodium ions penetrating into the oxide sensing layer, a barrier layer, which in one or more embodiments comprises a metal, is formed over the oxide layer, in one or more embodiments. Hafnium oxide (HfO$_2$) is a good barrier to ions that may penetrate from solution being tested into the dielectric layer 216.

For example, FIGS. 4 and 5 are cross-sectional views depicting at least a portion of illustrative biosensors 400 and 500, respectively, configured to reduce the drift effect caused by ions from a biological solution penetrating into a dielectric sensing layer of the biosensors, according to embodiments of the invention. With reference to FIG. 4, the biosensor 400 includes a lateral SOI BJT structure formed in a manner consistent with the biosensor 200 shown in FIG. 2. Specifically, the biosensor 400 includes n-type emitter and collector regions 206, 208 and a p-type intrinsic base region 210 between and laterally adjacent to the emitter and collector regions, formed on an SOI substrate (comprising BOX layer 204 and substrate 202). The biosensor 400 further comprises a sensing structure similar to the sensing structure incorporated in the biosensor 200 of FIG. 2, except for the addition of a barrier layer 402. The barrier layer 402, in one or more embodiments, is a layer which has the property of being a barrier to the diffusion of metallic ions and at the same time has a surface property of binding bio-molecules, formed over at least a portion of the dielectric layer 216. A profile of the layer 402 is configured to be conically-shaped (e.g., "funnel-shaped" or tapered), by virtue of the dielectric layer 216, insulating structures 212 and spacers 214 upon which layer 402 is formed, which beneficially serves as a receptacle 404 for providing a more effective confinement of bio-materials being tested/detected.

Similar to the biosensor 200 shown in FIG. 2, the shape and dimensions (e.g., thickness) of the dielectric layer 216, insulating structures 212 and sidewall spacers 214 will determine the profile of the barrier layer 402, including a depth of the receptacle 404. In one or more embodiments, layer 402 comprises gold, which, due to its chemistry, provides an easy method for functionalizing the sensing surface (402), tailoring the sensing surface for detecting a prescribed biological material or materials.

Likewise, with reference to FIG. 5, the biosensor 500 includes a lateral SOI BJT structure formed in a manner consistent with the biosensor 300 shown in FIG. 3. Specifically, the biosensor 500 includes n-type emitter and collector regions 206, 208 and a p-type intrinsic base region 210 between and laterally adjacent to the emitter and collector regions, formed on an SOI substrate (comprising BOX layer 204 and substrate 202). The biosensor 500 further comprises a sensing structure similar to the sensing structure incorporated in the biosensor 300 of FIG. 3, except for the addition of a layer 402, which has the property of being a barrier to diffusion of metallic ions and at the same time has a surface property of binding bio-molecules, formed over at least a portion of the dielectric layer 216. In comparison to the biosensor 400 shown in FIG. 4, the sensing structure of the biosensor 500 has a more stepped profile, resulting in a deeper receptacle 502, at least in part by virtue of the dielectric layer 216, first and second insulating structures 212 and 302, respectively, and sidewall spacers 214 upon which the barrier layer is formed. Similar to the biosensor 300 shown in FIG. 3, the shape and dimensions (e.g., thickness) of the dielectric layer 216, first and second insulating structures 212, 302, and sidewall spacers 214 will determine the profile of the layer 402, including a depth of the receptacle 502. In one or more embodiments, the layer 402 comprises gold.

Figure 6:
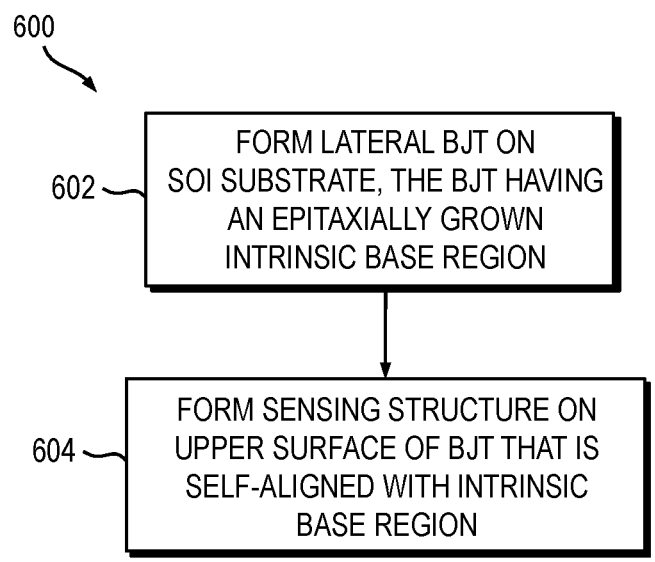
FIG. 6 is a flow diagram depicting steps of an illustrative method for forming a biosensor, according to embodiments of the present invention.

FIG. 6 is a flow diagram depicting steps of an illustrative method 600 for forming a biosensor, according to one or more embodiments of the invention. In step 602, a lateral BJT structure is formed on an SOI substrate. In this embodiment, the BJT device includes an epitaxially grown intrinsic base region. In step 604, a sensing structure is formed on at least a portion of an upper surface of the BJT structure, the sensing structure being self-aligned with the intrinsic base region. Making the sensing structure self-aligned with the intrinsic base region beneficially results in reduced device area and less parasitic capacitance.

By way of example only and without limitation, FIGS. 7A through 14B are top plan and cross-sectional views depicting exemplary processing steps/stages in the fabrication of exemplary biosensors, comprising a lateral SOI NPN BJT, according to embodiments of the invention; FIGS. 7A-8C are top plan and corresponding cross-sectional views depicting at least a portion of exemplary processing stages in the formation of an exemplary lateral SOI BJT structure of the biosensor, and FIGS. 9A-14B are top plan and cross-sectional views depicting at least a portion of exemplary processing stages in the formation of sensing structures of the biosensor.

Although the overall fabrication method and the structures formed thereby are entirely novel, certain individual processing steps required to implement the method may utilize conventional semiconductor fabrication techniques and conventional semiconductor fabrication tooling. These techniques and tooling will already be familiar to one having ordinary skill in the relevant arts given the teachings herein. Moreover, many of the processing steps and tooling used to fabricate semiconductor devices are also described in a number of readily available publications, including, for example: P. H. Holloway et al., *Handbook of Compound Semiconductors: Growth, Processing, Characterization, and Devices*, Cambridge University Press, 2008; and R. K. Willardson et al., *Processing and Properties of Compound Semiconductors*, Academic Press, 2001, which are both hereby incorporated herein by reference in their entireties for all purposes. It is emphasized that while some individual processing steps are set forth herein, those steps are merely illustrative, and one skilled in the art may be familiar with several equally suitable alternatives that would also fall within the scope of the invention.

It is to be appreciated that the various layers and/or regions shown in the accompanying figures may not be drawn to scale. Furthermore, one or more semiconductor layers of a type commonly used in such integrated circuit devices may not be explicitly shown in a given figure for ease of explanation. This does not imply that the semiconductor layer(s) not explicitly shown are omitted in the actual integrated circuit device.

Figure 7A:
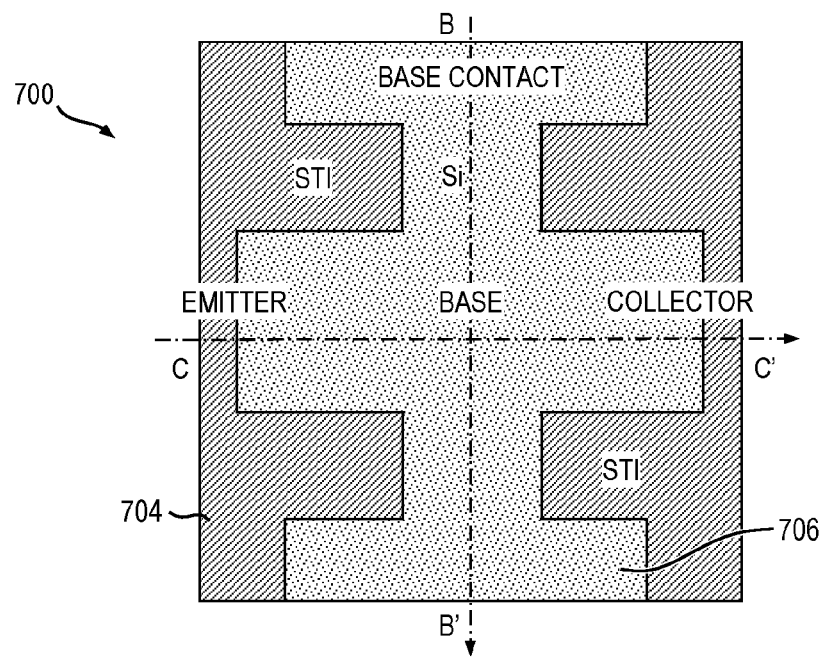
Figure 7B:
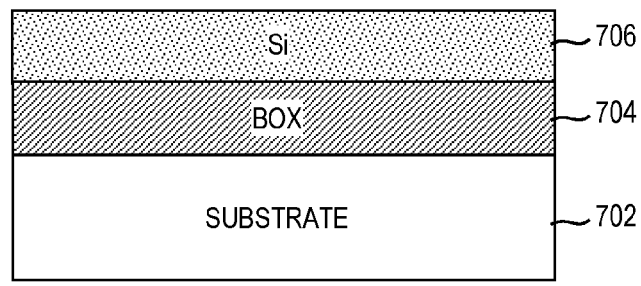
Figure 7C:
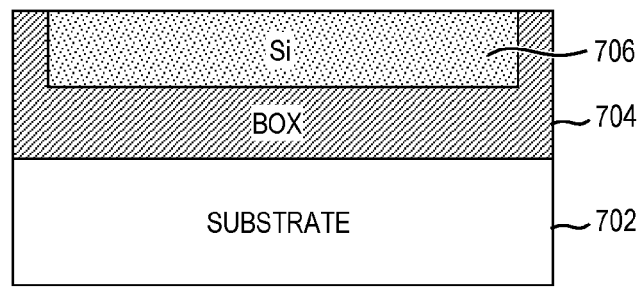

Reference is now made to FIGS. 7A-7C, where FIG. 7A is a top plan view of the formation of an SOI structure 700, according to an embodiment of the invention; FIGS. 7B and 7C are cross-sectional views of the structure of FIG. 7A, taken along lines B-B' and C-C', respectively. More particularly, FIGS. 7A-7C depict the formation of an SOI structure 700. The SOI structure 700 includes a substrate 702, which is commonly formed of single-crystal silicon (e.g., having a <100> or <111> crystal orientation), although suitable alternative materials may also be used, such as, but not limited to, germanium, silicon germanium, silicon carbide, gallium arsenide, gallium nitride, or the like. Next, a buried oxide (BOX) layer 704, such as, for example, a layer of silicon dioxide (SiO$_2$) or similar insulating material, is formed on at least a portion of an upper surface of the substrate 702. A silicon device layer 706, which may be referred to as an SOI layer, is then formed on at least a portion of an upper surface of the BOX layer 704. SOI wafers comprising the substrate 702, the BOX layer 704 and the silicon device layer 706, are commercially available. Commercially available SOI wafers can be used as a starting wafer for fabrication of the biosensor of the present invention. The silicon layer 706 is patterned, using standard lithography, to define areas to be used as an emitter, collector and base (including base contact leads) of the lateral SOI BJT structure, and then etched (e.g., using reactive ion etching (ME) or the like) to form shallow trench isolation (STI) regions in the SOI substrate.

Although not explicitly shown, during an STI formation process, a pattern of trenches is etched, as defined by exposed portions of a hard mask layer (formed on the silicon layer 706), through the silicon layer 706. One or more dielectric materials (e.g., silicon dioxide) are deposited, such as, for example, by chemical vapor deposition (CVD), to fill the trenches, and the excess dielectric material is removed using a planarization technique such as, for example, chemical-mechanical polishing (CMP), or the like. The STI regions provide electrical isolation between adjacent lateral BJT devices formed on the common substrate 702.

Figure 8A:
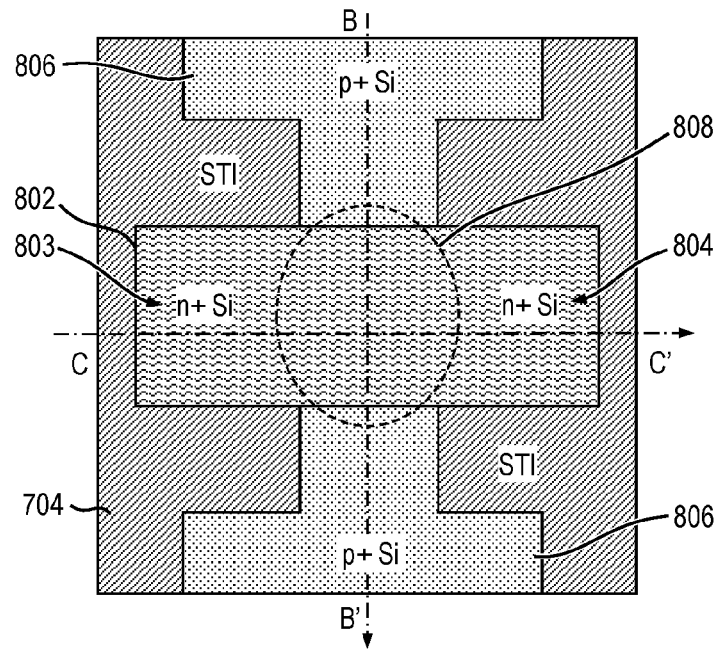
Figure 8B:
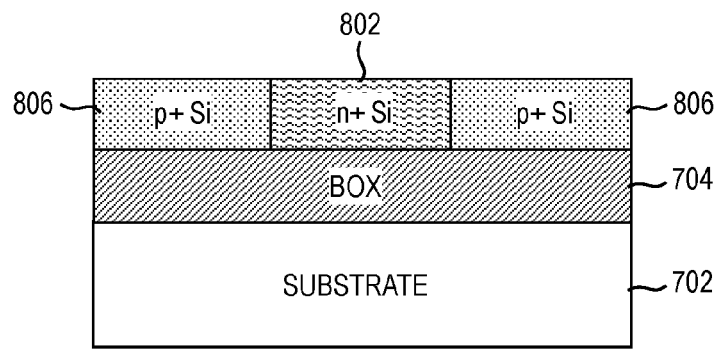
Figure 8C:
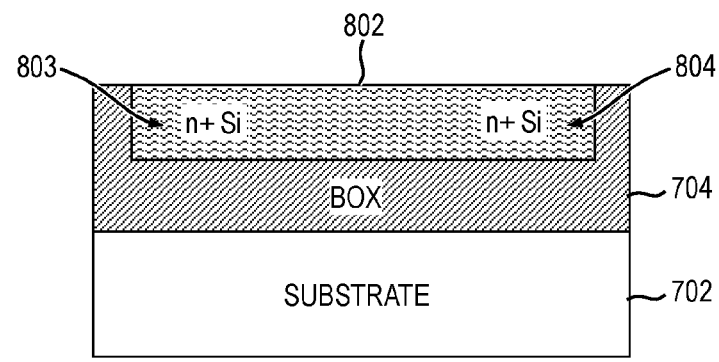

FIG. 8A is a top plan view depicting the formation of emitter, collector and extrinsic base regions of the lateral SOI BJT structure, according to an embodiment of the invention; FIGS. 8B and 8C are cross-sectional views of the structure of FIG. 8A, taken along lines B-B' and C-C', respectively. With reference to FIGS. 8A-8C, emitter (E) and collector (C) regions, 803 and 804, respectively, are formed in the silicon layer (706 in FIGS. 7A-7C) by doping a defined area 802 of the silicon layer with an impurity of a prescribed conductivity type and doping level. In this illustrative embodiment, the emitter and collector regions 803, 804 are doped with an n-type dopant (e.g., phosphorous or arsenic), although a p-type dopant (e.g., boron) may be similarly used, for example when forming a PNP BJT structure.

Next, the extrinsic base and base contact regions of the silicon layer are doped with an impurity having a conductivity type opposite that of the emitter and collector regions 803, 804. In this illustrative embodiment, assuming the emitter and collector regions are doped with an n-type dopant, the base and contact regions are doped with a p-type dopant (e.g., boron) to form p+ silicon areas 806. Doping of the base and contact regions is performed, in one or more embodiments, by using a suitable mask to expose areas of the silicon layer (706) except the emitter and collector regions, and introducing a suitable impurity, such as, for example, by an implantation process (e.g., ion implantation). A diffusion step is then performed, in one or more embodiments, to drive (i.e., distribute) the impurity into the silicon layer. An intersection 808 of the emitter/collector areas 803, 804 and the base/contact areas 806 will comprise both n-type and p-type dopants. However, the fact that the intersection 808 contains both n-type and p-type dopants at this stage of fabrication is immaterial because, as will be explained in the discussion relating to FIGS. 10A through 11C, the intersection 808 will be completely removed and an intrinsic base region will be formed in its place.

Figure 9A:
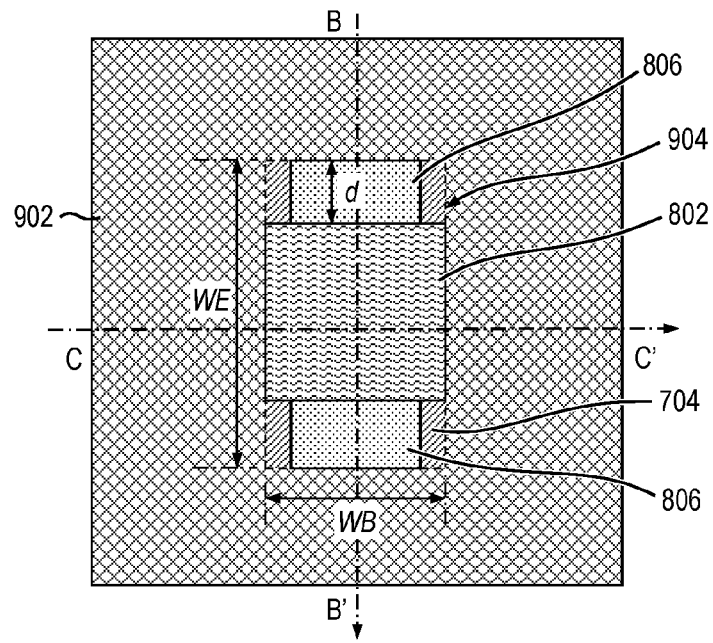
Figure 9B:
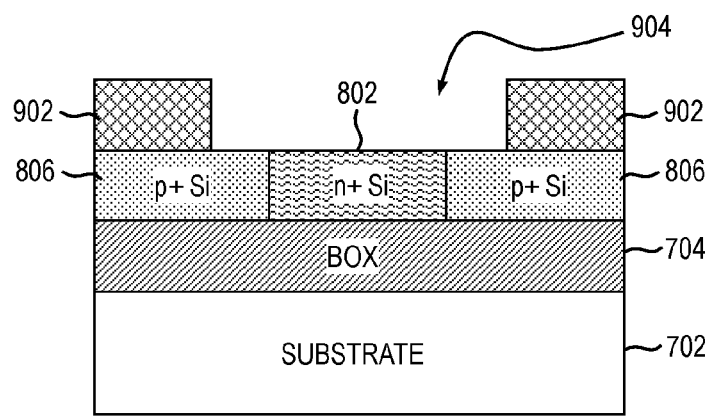
Figure 9C:
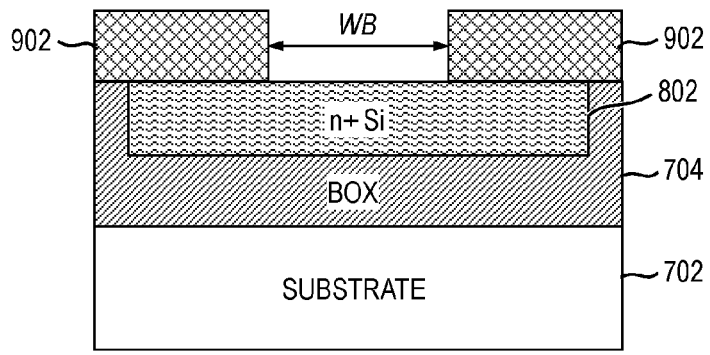

FIG. 9A is a top plan view depicting the formation of a base window, according to an embodiment of the invention; FIGS. 9B and 9C are cross-sectional views of the structure of FIG. 9A, taken along lines B-B' and C-C', respectively. With reference to FIGS. 9A-9C, an insulating (i.e., dielectric) layer 902 is formed on at least a portion of an upper surface of the structure, such as by using a standard deposition process (e.g., oxide deposition). In one or more embodiments, the insulating layer 902 comprises silicon dioxide, although suitable alternative materials are similarly contemplated. A base window (i.e., opening) 904 is formed in the insulating layer 902, such as, for example, by lithographic patterning and etching of the insulator layer on the silicon layer, in one or more embodiments.

In this illustrative embodiment, a size of the base window 904 is defined by dimensions WB and WE. The region of the silicon layer defined by the base window will be removed (in the steps discussed in FIG. 10) and an intrinsic base region will be formed in its place (as described below in conjunction with FIG. 11). WE, a dimension of the base window 904 along a device width direction, represents a distance between the two extrinsic base regions contacting the intrinsic base region (to be formed). WB represents a width of an intrinsic base region of the lateral SOI BJT structure; that is, the separation between emitter and collector regions of the lateral BJT. The value of WB will be dependent upon a dopant concentration of the intrinsic base region. In one or more embodiments, for a preferred device design, WB should be larger than a sum of the depletion layer width of the emitter-base junction and a depletion layer width of the collector-base junction. For example, for a base dopant concentration of about $1 \times 10^{18}$ cm$^{-3}$, WB should be larger than about 70 nm, and for a base dopant concentration of about $1 \times 10^{16}$ cm$^{-3}$, WB should be larger than about 700 nm.

Figure 10A:
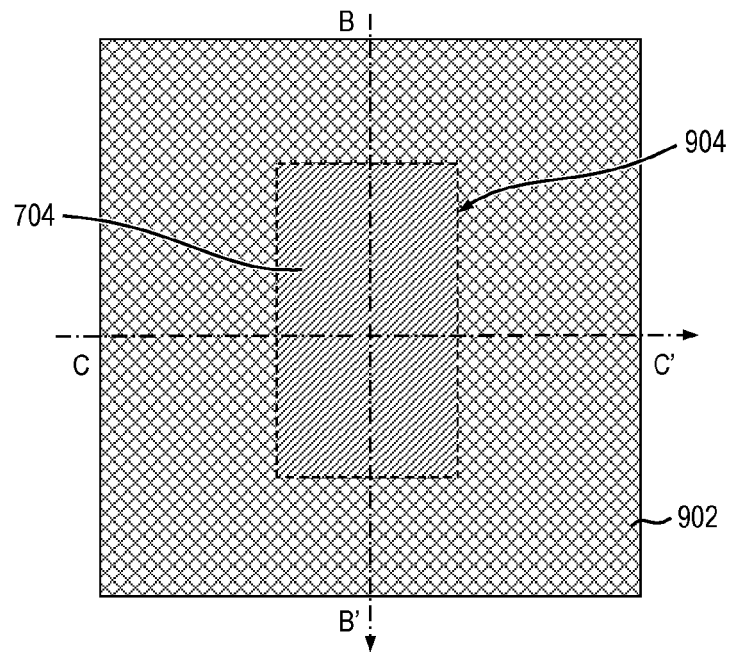
Figure 10B:
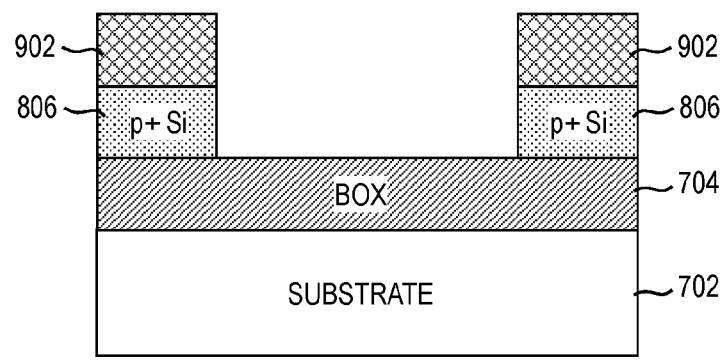

WE is made wider to include part of the extrinsic base regions to ensure there is no overlap of the relatively heavily doped emitter and collector regions (see emitter 803 and collector 804 in FIG. 10C) with the relatively heavily doped extrinsic base regions (see extrinsic base regions 806 in FIG. 10B). As indicated in FIG. 9A, WE is wider than the width of the emitter region 803 and collector region 804 by a length "d" at each end. The value of "d," in one or more embodiments, should be larger than an alignment tolerance used in the fabrication process to ensure no overlay of the relatively heavily doped emitter and collector regions with the relatively heavily doped extrinsic base regions. At the same time, the value of "d," in one or more embodiments, should be smaller than ½WB to ensure there is no void in the intrinsic base region, which is formed in a subsequent epitaxial growth step (to be discussed in conjunction with FIG. 11).

Figure 10C:
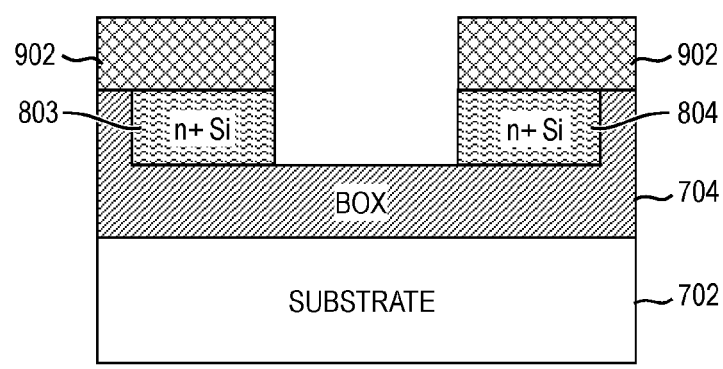

FIGS. 10A-10C depict a step of recessing the silicon defined by the base window opening 904 down to the BOX layer 704, according to an embodiment of the invention; FIG. 10A is a top plan view depicting the silicon recession; FIGS. 10B and 10C are cross-sectional views of the structure of FIG. 10A, taken along lines B-B' and C-C', respectively. Specifically, with reference to FIGS. 10A-10C, the silicon in the base region defined by window 904 is recessed down to the BOX layer 704. Recessing the silicon can be accomplished, in one or more embodiments, using an etching process, such as, for example, reactive ion etching (RIE), or the like. Preferably, an etchant is selected that has a significantly higher etch rate for silicon compared to the etch rate for oxide; that is, an etchant is employed having a greater affinity for silicon than for oxide. In this manner, the BOX layer 704 will serve as an etch-stop layer.

Figure 11A:
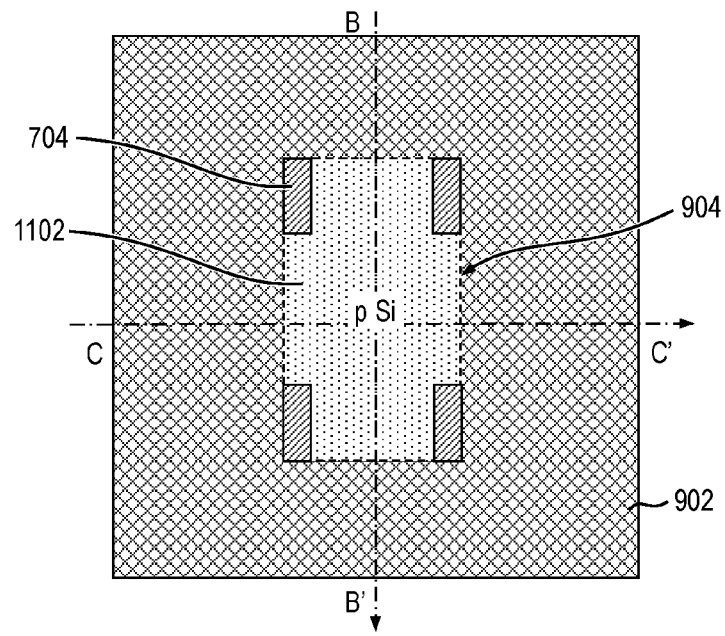
Figure 11B:
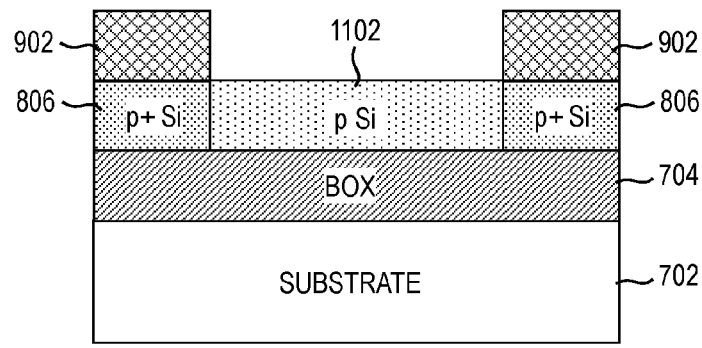
Figure 11C:
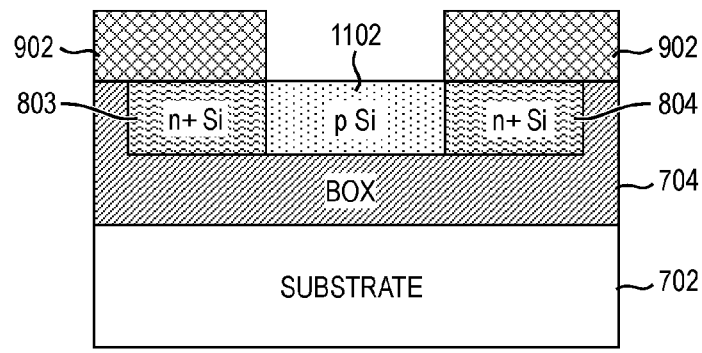

FIG. 11A is a top plan view depicting the formation of an intrinsic base region of the lateral SOI BJT structure, according to an embodiment of the invention; FIGS. 11B and 11C are cross-sectional views of the structure of FIG. 11A, taken along lines B-B' and C-C', respectively. With reference to FIGS. 11A-11C, an intrinsic base region 1102 is epitaxially grown, in situ, from doped silicon germanium (SiGe), or silicon or another material(s), in an intrinsic base area defined by the base window 904. The intrinsic base region 1102 is grown using exposed vertical surfaces (i.e., sidewalls) of the emitter and collector regions 803, 804, and the extrinsic base regions 806 as a seed. The intrinsic base region 1102 and the exposed base contacts 806 are electrically connected through overgrowth of the epitaxial, in-situ doped based region 1102, in one or more embodiments.

The resulting intrinsic base region 1102 will have a conductivity type that is opposite the conductivity type of the emitter and collector regions 803, 804, so as to form base-emitter and base-collector p-n junctions of the BJT structure. During operation of the exemplary lateral SOI BJT structure, the emitter-base junction is forward-biased and the collector-base junction is zero or reverse-biased for proper functioning of the BJT device. In this illustrative embodiment, the emitter and collector are formed of n-type conductivity material while the base is formed of p-type conductivity material, and therefore the lateral SOI BJT may be considered an NPN device. In other embodiments, the emitter and collector may be formed of a p-type conductivity material and the base formed of an n-type conductivity material, thereby resulting in a PNP BJT device.

The remaining insulating layer 902 above the emitter and collector regions 803 and 804, respectively, form an opening of a sensing structure that is self-aligned with the intrinsic base region 1102 and enables more effective confinement of biomaterials (especially liquids) to be detected, as previously described.

FIG. 12A is a top plan view depicting the formation of dielectric spacers in the sensing structure, according to an embodiment of the invention; FIGS. 11B and 11C are cross-sectional views of the structure of FIG. 11A, taken along lines B-B' and C-C', respectively. In one or more embodiments, the spacers are formed by first depositing a layer of dielectric material on at least a portion of an upper surface of the sensing structure, including the insulating layer 902 and within the opening 904 (i.e., over at least a portion of the intrinsic base region 1102 exposed through the opening 904). Reactive ion etching (ME) is then performed to remove the dielectric material on the horizontal surfaces of the sensing structure—that is, the insulating layer 902 and intrinsic base region 1102—leaving dielectric material on the exposed vertical surfaces (i.e., sidewalls) of the insulating layer 902 to thereby form dielectric sidewall spacers 1202. The sidewall spacers 1202 surround a perimeter of the opening 904 of the intrinsic base region 1102.

The initial size (i.e., drawn size) of the intrinsic base region 1102 is represented by the dimensions, WE and WB, as previously stated, which are defined by lithography. A cross-sectional thickness of the insulating layer 902, in conjunction with a horizontal thickness of the dielectric spacers 1202 near an upper surface of the intrinsic base region 1102, can be used to control an area of the exposed intrinsic base region 1102, in accordance with one or more embodiments of the invention. More particularly, by using a combination of a relatively thick insulating layer 902 and relatively thick dielectric spacers 1202, the final dimensions, WE' and WB', of the exposed intrinsic base region 1102 are configured to be in the nanometer regime. By way of example only and without limitation, if WB is selected to be 45 nanometers (nm) and the spacers 1202 are 20 nm in thickness, the final exposed opening of the intrinsic base region WB' would be 5 nm (i.e., 45 nm−2×20 nm=5 nm). With the dimensions WE' and/or WB' of the exposed intrinsic base region 1102 on the order of nanometers in size, the resulting biosensor device is suitable for sensing single biological molecules such as, but not limited to, DNA.

Figure 13A:
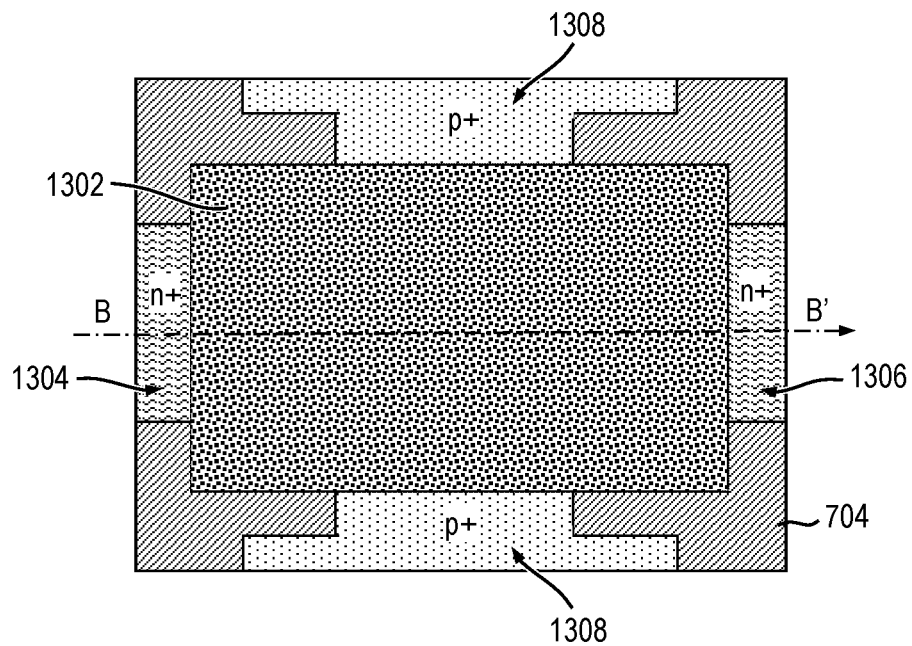
Figure 13B:
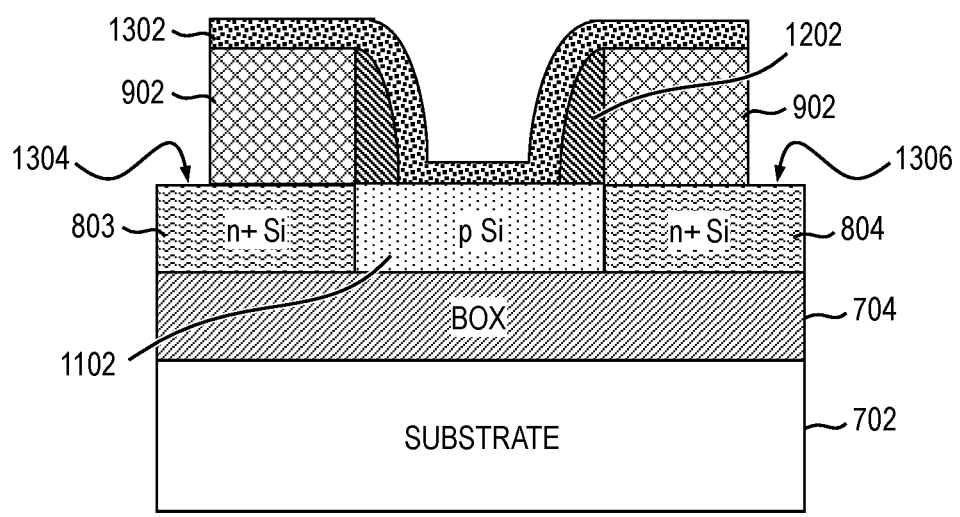

With reference now to FIGS. 13A and 13B, formation of a dielectric sensing layer is depicted, in accordance with an embodiment of the invention; FIG. 13A is a top plan view of the illustrative sensing structure and FIG. 13B is a cross-sectional view of the structure shown in FIG. 13A taken along line B-B'. Specifically, a dielectric sensing layer 1302, which in one or more embodiments comprises an oxide, is deposited on at least a portion of the upper surface of the biosensor structure (that is, over the insulating layer 902, the dielectric sidewall spacers 1202 and the exposed intrinsic base region 1102. A surface property of the sensing layer 1302 is configured to make the sensing layer sensitive to biological molecules. More particularly, the sensing layer 1302 is modified, in one or more embodiments, to bind to bio-molecules. The charges generated by bound bio-molecules present on the surface of the modified sensing layer 1302 induce image charges in the intrinsic base region 1102, causing an increase in electron current flowing from the emitter region 803 to the collector region 804.

In one or more embodiments, the sensing layer 1302 comprises a high-dielectric constant (high-k) insulating material, such as, for example, hafnium oxide ($HfO_2$), tantalum oxide ($Ta_2O_5$), or dual-layer silicon dioxide ($SiO_2$)/high-k film. The sensing layer 1302, in one or more embodiments, may alternatively comprise a multi-layer thin-film structure including at least one insulator layer and at least one metal layer, with the metal layer being in contact with the environmental condition/material being sensed and the insulating layer being in direct contact with the intrinsic base region 1102 of the sensing BJT device. As previously explained, the metal layer helps reduce or eliminate long-term drift issues caused by certain materials (e.g., NaCl) penetrating into the dielectric sensing layer. The metal layer of the dual-layer insulator/metal sensing layer 1302, in one or more embodiments, can be, for example, titanium nitride (TiN), gold, tungsten, platinum, or the like, and the insulating layer can be, for example, silicon nitride, silicon dioxide, nitride, or the like. The sensing layer 1302 is formed, in one or more embodiments, using a deposition technique, such as, for example, atomic layer deposition (ALD), CVD, sputtering, or the like, although other methods of forming the sensing layer are similarly contemplated.

A profile of the sensing layer 1302 is configured in the shape of a "funnel," by virtue of the insulating layer 902 and spacers 1202 upon which the dielectric layer is formed, which beneficially serves as a containing structure (i.e., receptacle) for more effectively holding bio-materials being tested/detected, especially liquids. Furthermore, the containing structure is beneficially self-aligned with the intrinsic base region 1102, as previously explained. The dimensions and/or shape of the insulating layer 902 and sidewall spacers 1202 (e.g., thickness) will determine the profile of the sensing layer 1302, including a depth of the containing structure. It is to be appreciated that embodiments of the invention are not limited to any specific dimensions and/or shapes of the insulating layer 902 and spacers 1202, and thus the sensing layer 1302.

Also shown in FIGS. 13A and 13B, patterning and etching (e.g., ME) of the dielectric sensing layer 1302 and insulating layer 902 is performed to thereby expose an emitter contact area 1304 of the emitter region 803, a collector contact area 1306 of the collector region 804, and base contact areas 1308 of the extrinsic base region. The exposed contact areas 1304, 1306 and 1308 provide electric access to the emitter, collector and base regions, respectively, of the underlying BJT structure.

Figure 14A:
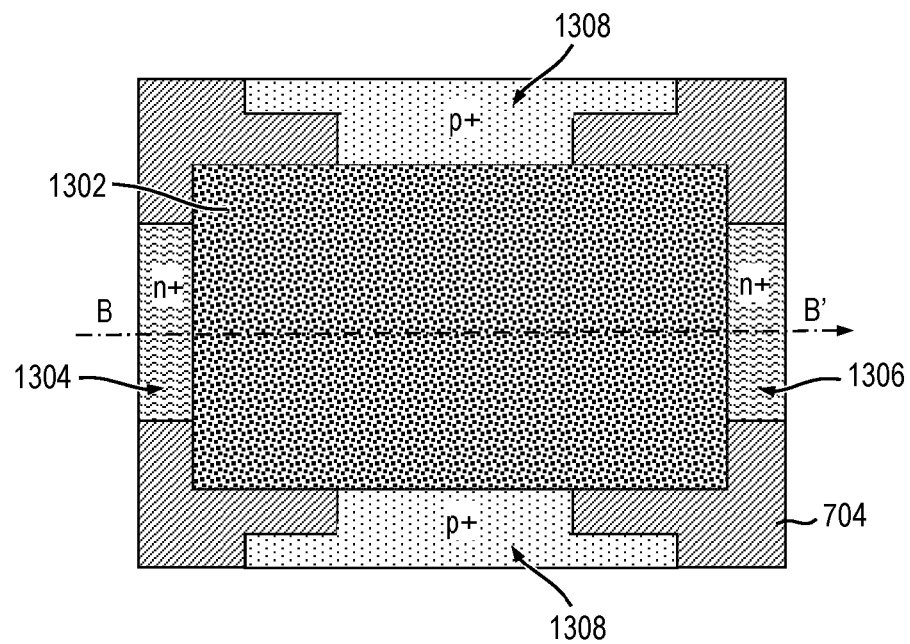
Figure 14B:
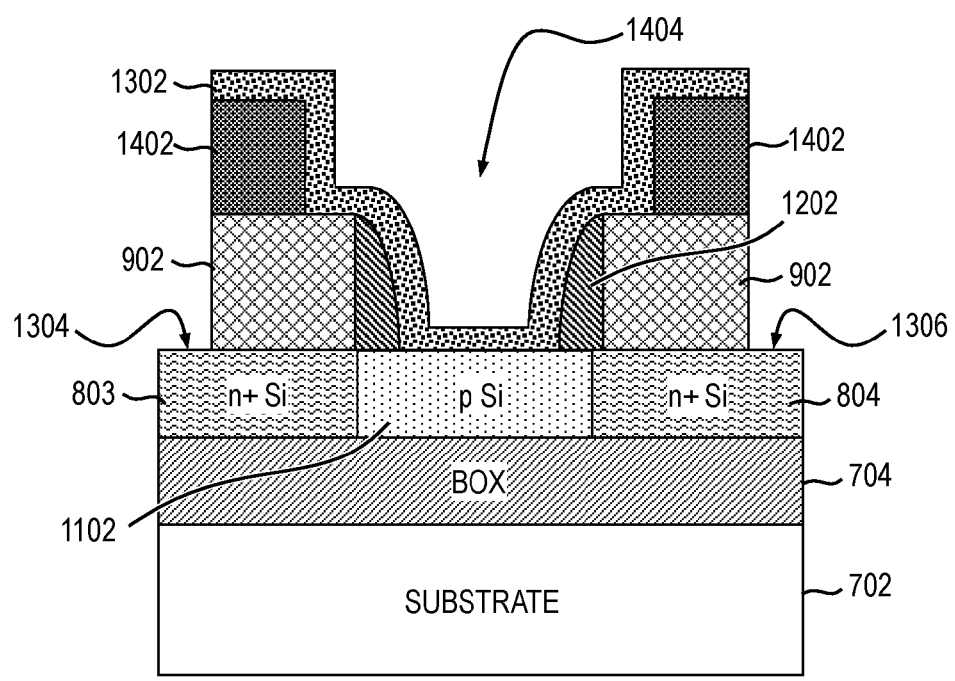

FIGS. 14A and 14B depict the formation of a dielectric sensing layer, in accordance with another embodiment of the invention; FIG. 14A is a top plan view of the illustrative sensing structure and FIG. 14B is a cross-sectional view of the structure shown in FIG. 14A taken along line B-B'. The exemplary biosensor shown in FIGS. 14A and 14B is similar to the illustrative biosensor shown in FIGS. 13A and 13B, except that the sensing structure of the biosensor shown in FIGS. 14A and 14B includes a sensing structure that is deeper and more steeply tapered compared to the sensing structure of the biosensor of FIGS. 13A and 13B. Specifically, with reference to FIGS. 14A and 14B, following the formation of the dielectric spacers 1202 (FIGS. 12A-C), a second insulating (i.e., dielectric) layer 1402 is formed on at least a portion of an upper surface of the first insulating layer 902 using a deposition technique, such as, for example, atomic layer deposition (ALD), CVD, sputtering, or the like, although other methods of forming the second insulating layer are similarly contemplated. In one or more embodiments, the second insulating layer 1402 is formed of a material that can be preferentially etched with respect to the first insulating layer 902. For example, the first insulating layer 902 may comprise nitride and the second insulating layer 1402 may comprise oxide, according to one or more embodiments.

After depositing the second insulating layer 1402, a second window 1404, larger than the base window 904 (FIGS. 9A and 9B), is formed through the second insulating layer. In one or more embodiments, the second window 1404 is formed by patterning and etching the second insulating layer 1402 using an etchant that is preferential to the material used to form the second insulating layer and not the material forming the first insulating layer 902. The second window 1404 is positioned to surround the base window 904, so that the base window is completely enclosed within the second window.

Next, in a manner consistent with the formation of the sensing structure shown in FIGS. 13A and 13B, the dielectric sensing layer 1302 is deposited on at least a portion of the upper surface of the biosensor structure (that is, over at least portions of the second insulating layer 1402, the first insulating layer 902, the dielectric sidewall spacers 1202 and the exposed intrinsic base region 1102. A surface property of the sensing layer 1302 is configured to make the sensing layer sensitive to biological molecules. More particularly, the sensing layer 1302 is modified, in one or more embodiments, to bind to bio-molecules. The intrinsic base region 1102 is adapted to generate a sensing current or voltage which varies as a function of charges generated by bound bio-molecules present on the surface of the modified sensing layer 1302.

Compared to the profile of the sensing layer 1302 in the illustrative sensing structure depicted in FIGS. 13A and 13B, the sensing layer 1302 in the exemplary sensing structure shown in FIGS. 14A and 14B is deeper, due to the addition of the second insulating layer. As a result, the sensing structure of the exemplary biosensor shown in FIGS. 14A and 14B will contain a larger volume of bio-materials being tested. The dimensions and/or shape of the second insulating layer 1402, the first insulating layer 902 and sidewall spacers 1202 (e.g., thickness) will determine the profile of the sensing layer 1302, including a depth of the containing structure. It is to be appreciated that embodiments of the invention are not limited to any specific dimensions and/or shapes of the first and second insulating layers 902, 1402 and spacers 1202, and thus the sensing layer 1302.

Moreover, in a manner consistent with the fabrication of the biosensor depicted in FIGS. 13A and 13B, patterning and etching (e.g., ME) of the dielectric sensing layer 1302 and first and second insulating layers 902, 1402 is performed on the biosensor of FIGS. 14A and 14B to thereby expose the emitter contact area 1304 of the emitter region 803, the collector contact area 1306 of the collector region 804, and the base contact areas 1308 of the extrinsic base region. The exposed contact areas 1304, 1306 and 1308 provide electric access to the emitter, collector and base regions, respectively, of the underlying BJT structure, as previously stated.

It is to be appreciated that although the exemplary biosensor shown in FIGS. 7A-14B is fabricated with a self-aligned epitaxially grown intrinsic base region, one or more embodiments of the invention may similarly contemplate a sensor structure formed without a self-aligned intrinsic base region. More particularly, the novel device concept of forming a "conically-shaped" sensing structure on top of the intrinsic base can be similarly applied to a non-self-aligned intrinsic base region, according to one or more embodiments of the invention. In this regard, fabrication of a BJT structure having a non-self-aligned intrinsic base will involve modification of one or more process steps in the process flow shown in FIGS. 7A-14B, with the intrinsic base region being formed by simple masked ion implantation or the like, rather than by recessing the silicon region (e.g., region 808 in FIGS. 8A-8C) followed by epitaxial regrowth, as will become apparent to those skilled in the art.

Figure 15:
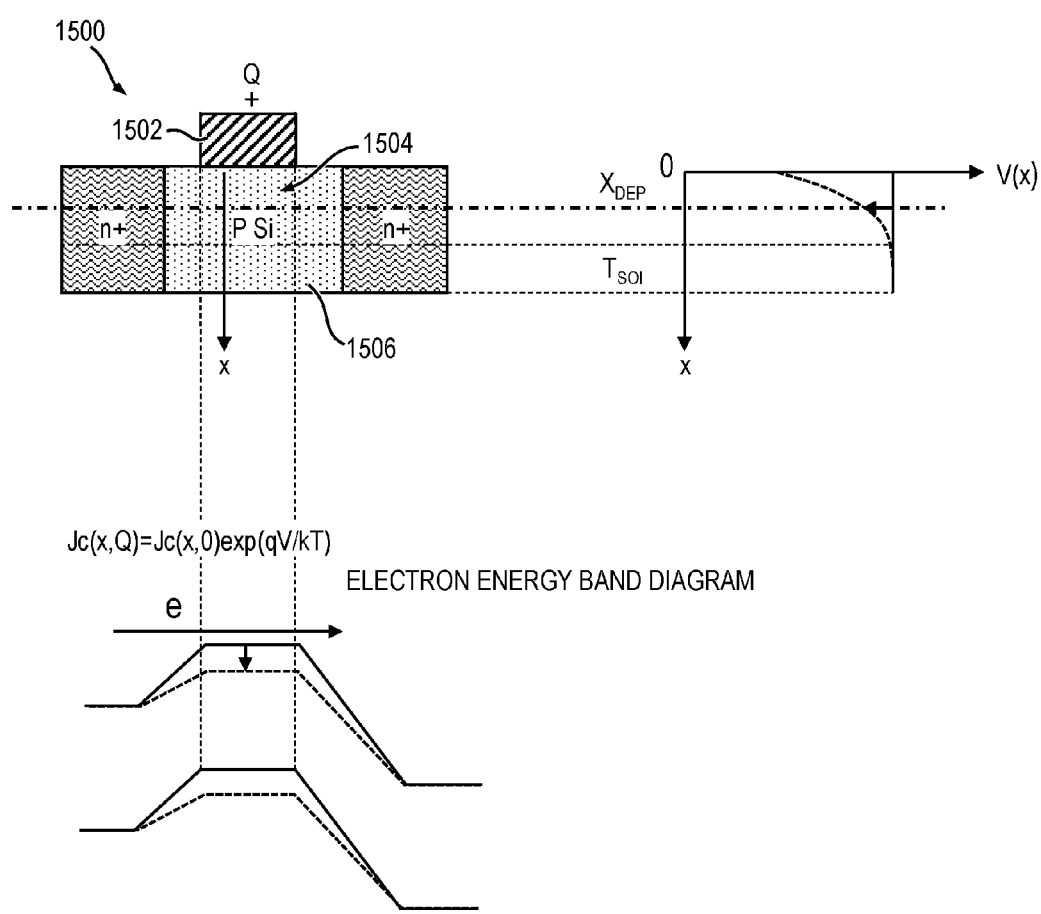
FIG. 15 conceptually depicts an exemplary approach for optimizing a sensitivity of the biosensor through careful design of the lateral SOI BJT structure in the biosensor, according to one or more embodiments of the present invention.

FIG. 15 conceptually depicts an exemplary approach for optimizing the sensitivity of a biosensor 1500 through careful design of the lateral SOI BJT structure in the biosensor, according to one or more embodiments of the invention. With reference to FIG. 15, positive charge, Q, bounded to the surface of an oxide sensing layer 1502 of the biosensor 1500 induces a depletion layer 1504 proximate the upper surface of an intrinsic base region 1506 of the lateral SOI BJT structure. A thickness (i.e., depth), $X_{DEP}$, of the depletion layer 1504 will be a function of an intrinsic base doping concentration, $N_B$, as evidenced by the following expression for charge Q:

$$Q = qN_B \cdot X_{DEP}, X_{DEP} < T_{SOI},$$

where q represents the magnitude of an electron charge and $T_{SOI}$ represents a thickness of the silicon layer of the SOI substrate; that is, the positive charge Q bounded on the surface of the oxide sensing layer 1502 induces an image charge of the same magnitude as Q in the depletion layer 1504.

Within the depletion layer 1504, the emitter-base (E-B) potential barrier is reduced, leading to an exponential increase in collector current ($I_{C1}$). Outside of the depletion layer 1504, collector current density is not affected ($I_{C2}$). To maximize the biosensor sensitivity, the depletion layer thickness should be comparable to SOI layer thickness ($X_{DEP} \sim T_{SOI}$). Sensitivity reduces when the base is fully depleted.

Consider the following derivation for computing collector current sensitivity, $I_C(Q)/I_C(0)$, where $I_C(Q)$ is the collector current when there is a positive charge Q bounded on the surface of oxide sensing layer 1502 and $I_C(0)$ is the collector current when there is no positive charge bounded on the surface of oxide sensing layer 1502:

$$V_S = \frac{qN_B}{2 \cdot \varepsilon_0 \varepsilon_{Si}} \cdot X_{DEP}^2$$

$$I_C(Q) = I_{C1} + I_{C2}$$

$$I_{C1} = I_C(0) \cdot \frac{X_{DEP}}{T_{SOI}} \cdot \frac{\int_0^{V_S} e^{qV/kT} dV}{\int_0^{V_S} dV} = I_C(0) \cdot \frac{X_{DEP}}{T_{SOI}} \cdot \frac{kT}{qV_S} \cdot (e^{qV_S/kT} - 1)$$

$$I_{C2} = I_C(0) \cdot \frac{T_{SOI} - X_{DEP}}{T_{SOI}}$$

$$\frac{I_C(Q)}{I_C(0)} = \frac{X_{DEP}}{T_{SOI}} \cdot \frac{kT}{qV_S} \cdot (e^{qV_S/kT} - 1) + \frac{T_{SOI} - X_{DEP}}{T_{SOI}},$$

where $V_S$ is the maximum voltage lowering in the base region caused by the positive chare Q bounded on the surface of the oxide sensing layer 1502, $N_B$ is the dopant concentration in the base region, q is the magnitude of an electron charge, $\varepsilon_0$ is vacuum permittivity constant, $\varepsilon S_i$ is the dielectric constant of silicon, $X_{DEP}$ is the thickness of the depletion layer in the base region, $I_{C1}$ is a component of collector current flowing in the depleted portion of the base, $I_{C2}$ is a component of collector current flowing in the non-depleted portion of the base, $I_C(Q)$ is a sum of $I_{C1}$ and $I_{C2}$, and $T_{SOI}$ is the thickness of the SOI layer. As previously stated, when the depletion layer thickness is made comparable to SOI layer thickness (i.e., $X_{DEP} \sim T_{SOI}$), the expression for sensitivity $I_C(Q)/I_C(0)$ reduces to the following expression:

$$\frac{I_C(Q)}{I_C(0)} = \frac{kT}{qV_S} \cdot (e^{qV_S/kT} - 1).$$

Figure 16:
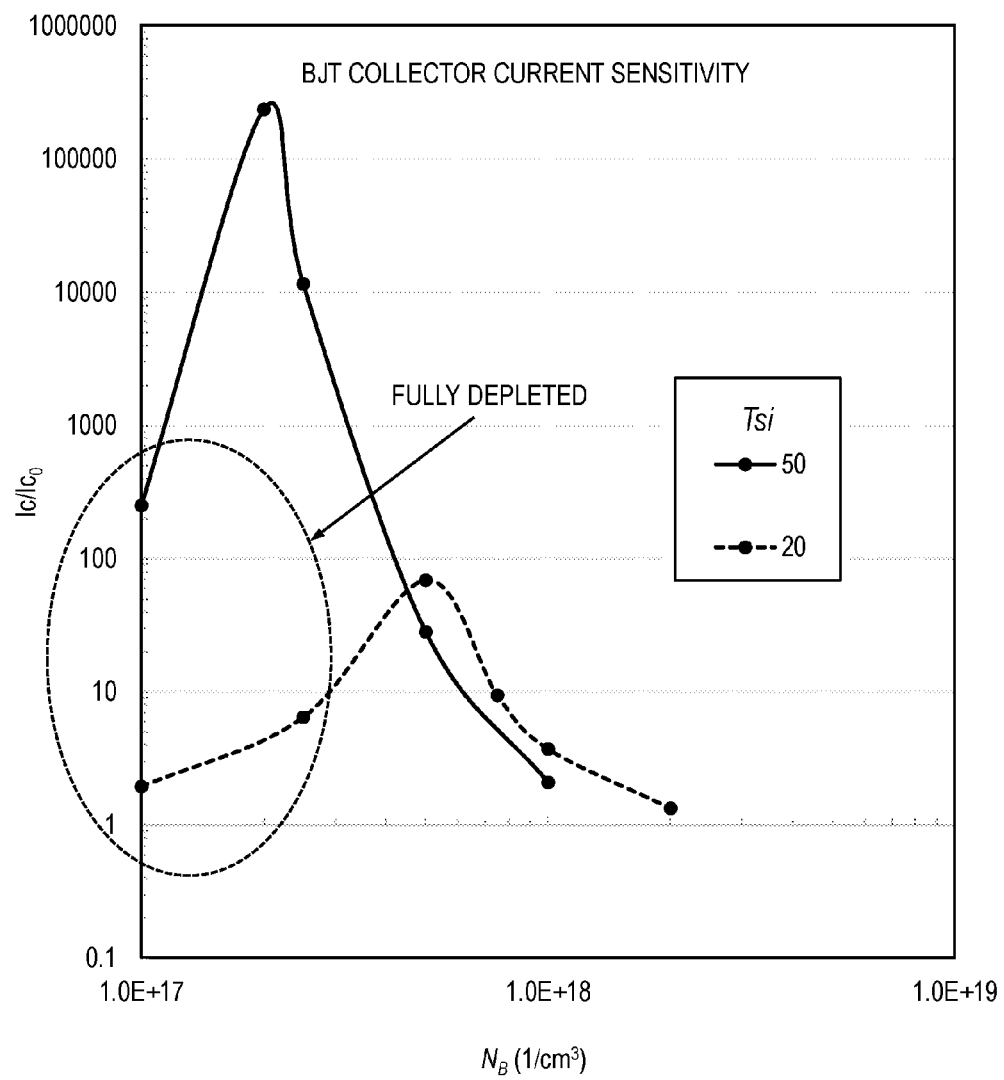
FIG. 16 is a graph depicting a comparison between illustrative lateral SOI BJT collector current sensitivities for two different thicknesses, namely, 20 nm and 50 nm, of the SOI layer, according to an embodiment of the present invention.

By way of example only and without limitation, FIG. 16 is a graph depicting a comparison between illustrative lateral SOI BJT collector current sensitivities for two different depletion layer thicknesses, namely, $X_{DEP}=20$ nm and 50 nm, according to an embodiment of the invention. For this illustrative embodiment, single charge detection is assumed using a sensing window opening of about 10 nm×10 nm. For a small opening area of 10 nm×10 nm, a single charge corresponds to a charge density of 1 e12/cm².

Simulation of sensing currents for this illustrative embodiment is made under the following conditions: emitter-base junction (diode) is forward biased at 0.6 V and collector current is monitored. The presence of the base contact enables the emitter-base junction to be forward-biased without requiring a reference electrode. The charges bound to the oxide sensing layer on top of the intrinsic base region are capacitively coupled to the base and modulate the sensing collector current $I_C$.

As shown in FIG. 16, peak sensitivity for a given SOI thickness is achieved when the charge induces a fully depleted base from the top ($X_{DEP}=T_{SOI}$). In one or more embodiments, thicker SOI substrates can be designed with lighter doping concentration, $N_B$, for higher sensitivity. For example, with $T_{SOI}=50$ nm and $N_B=2e17/cm^3$, a peak sensitivity with collector current increase over 20,000 times can be expected.

A unified expression for collector current sensitivity $I_C(Q)/I_C(0)$ is as follows:

$$\frac{I_C(Q)}{I_C(0)} = \frac{\min(X_{DEP}, T_{SOI})}{T_{SOI}} \cdot \frac{kT}{qV_S} \cdot (e^{qV_S/kT} - 1) + \frac{T_{SOI} - \min(X_{DEP}, T_{SOI})}{T_{SOI}}$$

$$V_S = \frac{qN_B}{2 \cdot \varepsilon_0 \varepsilon_{Si}} \cdot \min(X_{DEP}, T_{SOI})^2$$

Table 1 below depicts collector current sensitivities $I_C(Q)/I_C(0)$ for various exemplary parameters associated with the lateral SOI BJT of a biosensor according to an illustrative embodiment, where $J_{C1}(0)$ refers to the collector current with the given base and emitter/collector concentrations, and $J_{C1}$ refers to the change in collector current due to the barrier reduction in the base region caused by external charges from the bio-materials.

TABLE 1

| $T_{Si}$ (nm) | Q (#/cm²) | $N_B$ (/cm³) | $X_{DEP}$ (nm) | $V_S$ (mV) | $J_{C1}/J_{C1}(0)$ | $I_C(Q)/I_C(0)$ |
|---|---|---|---|---|---|---|
| 50 | 1.0E+12 | 1.0E+17 | 100 | 1.9E+02 | 2.50E+02 | 250 |
| 50 | 1.0E+12 | 2.0E+17 | 50 | 3.9E+02 | 2.36E+05 | 235545 |
| 50 | 1.0E+12 | 2.5E+17 | 40 | 3.1E+02 | 1.44E+04 | 11534 |
| 50 | 1.0E+12 | 5.0E+17 | 20 | 1.5E+02 | 6.90E+01 | 28 |
| 50 | 1.0E+12 | 1.0E+18 | 10 | 7.7E+01 | 6.44E+00 | 2 |
| 20 | 1.0E+12 | 1.0E+17 | 100 | 3.1E+01 | 1.94E+00 | 2 |
| 20 | 1.0E+12 | 2.5E+17 | 40 | 7.7E+01 | 6.44E+00 | 6 |
| 20 | 1.0E+12 | 5.0E+17 | 20 | 1.5E+02 | 6.90E+01 | 69 |
| 20 | 1.0E+12 | 7.5E+17 | 13 | 1.0E+02 | 1.36E+01 | 9 |
| 20 | 1.0E+12 | 1.0E+18 | 10 | 7.7E+01 | 6.44E+00 | 4 |
| 20 | 1.0E+12 | 2.0E+18 | 5 | 3.9E+01 | 2.33E+00 | 1 |

The lateral SOI BJT structure included in the biosensor according to one or more embodiments of the invention has base contacts from the two sides of the base, as previously described. This device configuration enables elimination of the use of a separate reference electrode immersed in the liquid being sensed during sensing. This is a significant advantage since the monolithic integration of a separate reference electrode is very difficult. Moreover, a separate reference electrode immersed in the liquid being sensed tends to degrade with use and therefore creates reliability issues.

Given the discussion thus far, it will be appreciated that, in general terms, an exemplary biosensor sensor for detecting the presence of a biological material, according to an aspect of the invention, includes an SOI substrate, a BJT formed on at least a portion of the substrate, and a sensing structure formed on at least a portion of an upper surface of the BJT. The BJT includes an emitter region, a collector region and a self-aligned epitaxially grown intrinsic base region laterally adjacent to the emitter and collector regions. The sensing structure includes an opening, centered above and exposing the intrinsic base region, and at least one dielectric layer formed in the opening and contacting at least a portion of the intrinsic base region. The dielectric layer is configured to respond to charges in biological molecules, the charges being converted to a sensing signal by the BJT.

Given the discussion thus far, it will also be appreciated that an exemplary biosensor for detecting the presence of a biological material, according to another aspect of the invention, includes an SOI substrate, a lateral BJT formed on at least a portion of the substrate, and a sensing structure formed on at least a portion of an upper surface of the BJT. The BJT includes an emitter region, a collector region and a base region, the base region being formed between the emitter and collector regions and laterally adjacent thereto. The sensing structure includes at least one dielectric layer contacting at least a portion of the base region. The dielectric layer forms a conically-shaped receptacle and is configured to respond to charges in biological molecules, the charges being converted to a sensing signal by the BJT.

Given the discussion thus far, it will also be appreciated that an exemplary method for forming a biosensor for the detecting the presence of a biological material includes: forming a lateral BJT on at least a portion of an SOI substrate, the BJT including an emitter region, a collector region and a self-aligned epitaxially grown intrinsic base region adjacent to the emitter and collector regions; and forming a sensing structure on at least a portion of an upper surface of the BJT, the sensing structure including an opening, centered above and exposing the intrinsic base region, and at least one dielectric layer formed in the opening and contacting at least a portion of the intrinsic base region, the dielectric layer being configured to respond to charges in biological molecules.

At least a portion of the techniques of the present invention may be implemented in an integrated circuit. In forming integrated circuits, identical die are typically fabricated in a repeated pattern on a surface of a semiconductor wafer. Each die includes a device described herein, and may include other structures and/or circuits. The individual die are cut or diced from the wafer, then packaged as an integrated circuit. One skilled in the art would know how to dice wafers and package die to produce integrated circuits. Any of the exemplary circuits illustrated in the accompanying figures, or portions thereof, may be part of an integrated circuit. Integrated circuits so manufactured are considered part of this invention.

Those skilled in the art will appreciate that the exemplary structures discussed above can be distributed in raw form (i.e., a single wafer having multiple unpackaged chips), as bare dies, in packaged form, or incorporated as parts of intermediate products or end products that benefit from having sensor devices therein formed in accordance with one or more embodiments of the invention.

An integrated circuit in accordance with aspects of the present disclosure can be employed in essentially any application and/or electronic system involving sensors that can detect and provide relevant environmental information, such as, but not limited to, biological molecules, radiation, chemical materials, inorganic particles, etc. Suitable systems for implementing embodiments of the invention may include, but are not limited to, biosensors. Systems incorporating such integrated circuits are considered part of this invention. Given the teachings of the present disclosure provided herein, one of ordinary skill in the art will be able to contemplate other implementations and applications of embodiments of the invention.

The illustrations of embodiments of the invention described herein are intended to provide a general understanding of the various embodiments, and they are not intended to serve as a complete description of all the elements and features of apparatus and systems that might make use of the circuits and techniques described herein. Many other embodiments will become apparent to those skilled in the art given the teachings herein; other embodiments are utilized and derived therefrom, such that structural and logical substitutions and changes can be made without departing from the scope of this disclosure. The drawings are also merely representational and are not drawn to scale. Accordingly, the specification and drawings are to be regarded in an illustrative rather than a restrictive sense.

Embodiments of the invention are referred to herein, individually and/or collectively, by the term "embodiment" merely for convenience and without intending to limit the scope of this application to any single embodiment or inventive concept if more than one is, in fact, shown. Thus, although specific embodiments have been illustrated and described herein, it should be understood that an arrangement achieving the same purpose can be substituted for the specific embodiment(s) shown; that is, this disclosure is intended to cover any and all adaptations or variations of various embodiments. Combinations of the above embodiments, and other embodiments not specifically described herein, will become apparent to those of skill in the art given the teachings herein.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. Terms such as "above" and "below" are used to indicate relative positioning of elements or structures to each other as opposed to relative elevation.

The corresponding structures, materials, acts, and equivalents of all means or step-plus-function elements in the claims below are intended to include any structure, material, or act for performing the function in combination with other claimed elements as specifically claimed. The description of the various embodiments has been presented for purposes of illustration and description, but is not intended to be exhaustive or limited to the forms disclosed. Many modifications and variations will be apparent to those of ordinary skill in the art without departing from the scope and spirit of the invention. The embodiments were chosen and described in order to best explain the principles of the invention and the practical application, and to enable others of ordinary skill in the art to understand the various embodiments with various modifications as are suited to the particular use contemplated.

The abstract is provided to comply with 37 C.F.R. §1.72 (b), which requires an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the appended claims reflect, inventive subject matter lies in less than all features of a single embodiment. Thus the following claims are hereby incorporated into the Detailed Description, with each claim standing on its own as separately claimed subject matter.

Given the teachings of embodiments of the invention provided herein, one of ordinary skill in the art will be able to contemplate other implementations and applications of the techniques of embodiments of the invention. Although illustrative embodiments of the invention have been described herein with reference to the accompanying drawings, it is to be understood that embodiments of the invention are not limited to those precise embodiments, and that various other changes and modifications are made therein by one skilled in the art without departing from the scope of the appended claims.

What is claimed is:

1. A biosensor, comprising:
   a silicon-on-insulator (SOI) substrate;
   a lateral bipolar junction transistor (BJT) formed on at least a portion of the substrate, the BJT including an emitter region, a collector region and a base region, the base region being formed between the emitter and collector regions and laterally adjacent thereto; and
   a sensing structure formed on at least a portion of an upper surface of the BJT, the sensing structure including at least one dielectric layer contacting at least a portion of the base region, the dielectric layer forming a receptacle for confining a biological molecule being tested and being configured to respond to charges in biological molecules, the charges being converted to a sensing signal by the BJT.

2. The biosensor of claim 1, wherein the BJT comprises at least one emitter terminal in electrical contact with the emitter region, at least one collector terminal in electrical contact with the collector region, and at least one base terminal in electrical contact with the base region, the base terminal being in a same plane as the emitter and collector terminals.

3. The biosensor of claim 1, wherein the sensing structure comprises:
   a first insulating structure formed on at least a portion of an upper surface of the BJT, proximate the emitter and collector regions, the first insulating structure including an opening surrounding at least a portion of the base region through which the base region is exposed; and
   dielectric spacers formed on sidewalls of the first insulating structure and defining the opening in the first insulating structure exposing the base region, the dielectric layer being formed on at least a portion of the first insulating structure and dielectric spacers such that a profile of the dielectric layer forms the receptacle for confining the biological molecule being tested.

4. The biosensor of claim 1, wherein the sensing structure further comprises a barrier layer formed on an upper surface of at least a portion of the dielectric layer, the barrier layer being configured to reduce a drift effect caused by ions from a biological molecule being tested penetrating into the dielectric layer of the sensing structure.

5. The biosensor of claim 1, wherein the dielectric layer in the sensing structure comprises a composite structure including a bottom dielectric layer, a top dielectric layer and an electrically conductive layer sandwiched between the top and bottom dielectric layers, the top dielectric layer being modified to bind to biological molecules.

6. The biosensor of claim 2, wherein the base terminal is positioned perpendicular to at least one of the emitter and collector terminals.

7. The biosensor of claim 3, wherein a shape of the receptacle is configured as a function of at least a cross-sectional thickness of at least one of the first insulating structure and the dielectric spacers.

8. The biosensor of claim 3, wherein the base region of the BJT is self-aligned with the opening in the first insulating structure.

9. The biosensor of claim 3, wherein the sensing structure further comprises a second insulating structure formed on an upper surface of at least a portion of the first insulating structure, the dielectric layer being formed on at least a portion of the first and second insulating structures and dielectric spacers so as to increase a depth of the receptacle above an upper surface of the base region.

10. The biosensor of claim 4, wherein the barrier layer comprises a composite structure including a plurality of material layers, at least one of the material layers comprising a metal.

11. The biosensor of claim 10, wherein at least one layer of the composite structure comprises gold.

12. A method of forming a biosensor, the method comprising:
    forming a lateral bipolar junction transistor (BJT) on at least a portion of a silicon-on-insulator (SOI) substrate, the BJT including an emitter region, a collector region and a base region, the base region being formed between the emitter and collector regions and laterally adjacent thereto; and
    forming a sensing structure on at least a portion of an upper surface of the BJT, the sensing structure including at least one dielectric layer contacting at least a portion of the base region, the dielectric layer forming a receptacle for confining a biological molecule being tested and being configured to respond to charges in biological molecules, the charges being converted to a sensing signal by the BJT.

13. The method of claim 12, wherein forming the sensing structure comprises forming an opening in the sensing structure centered above and exposing the base region, and forming the at least one dielectric layer in the opening and contacting at least a portion of the base region.

14. The method of claim 12, wherein forming the sensing structure further comprises forming a barrier layer on an upper surface of at least a portion of the dielectric layer, the barrier layer being configured to reduce a drift effect caused by ions from a biological molecule being tested penetrating into the dielectric layer of the sensing structure.

15. The method of claim 12, wherein forming the BJT comprises forming at least one emitter terminal in electrical contact with the emitter region, at least one collector terminal in electrical contact with the collector region, and at least one base terminal in electrical contact with the base region, the base terminal being formed in a same plane as the emitter and collector terminals.

16. The method of claim 12, wherein forming the sensing structure comprises:
    forming a first insulating structure on at least a portion of an upper surface of the BJT, proximate the emitter and collector regions and surrounding the base region; and
    forming dielectric spacers on sidewalls of the first insulating structure, the dielectric spacers defining a perimeter of an opening exposing the base region, the dielectric layer being formed on at least a portion of the first insulating structure and dielectric spacers such that a profile of the dielectric layer forms the receptacle for confining the biological molecule being tested.

17. The method of claim 13, further comprising self-aligning the opening of the sensing structure with the base region.

18. The method of claim 14, wherein the barrier layer comprises a composite structure including a plurality of material layers, at least one of the material layers comprising a metal.

19. The method of claim 15, wherein the base terminal is positioned perpendicular to at least one of the emitter and collector terminals.

20. The method of claim 16, further comprising controlling a profile of the receptacle as a function of at least one of a cross-sectional thickness and a shape of at least one of the first insulating structure and the dielectric spacers.

* * * * *